US 9,095,668 B2

(12) United States Patent
Blackhurst et al.

(10) Patent No.: US 9,095,668 B2
(45) Date of Patent: *Aug. 4, 2015

(54) APPARATUS USED FOR HUMIDIFICATION OF GASES IN MEDICAL PROCEDURES

(75) Inventors: Michael Joseph Blackhurst, Auckland (NZ); Nina Caroline Batty, Auckland (NZ); Daniel John Smith, Auckland (NZ); Hussein Kadhum, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 13/531,423

(22) Filed: Jun. 22, 2012

(65) Prior Publication Data
US 2013/0072862 A1 Mar. 21, 2013

Related U.S. Application Data

(63) Continuation of application No. 10/398,099, filed as application No. PCT/NZ01/00226 on Oct. 15, 2001, now Pat. No. 8,206,337.

(30) Foreign Application Priority Data

Oct. 16, 2000 (NZ) .................................. 507553
Dec. 12, 2000 (NZ) .................................. 508850
Sep. 19, 2001 (NZ) .................................. 514314

(51) Int. Cl.
*A61M 37/00* (2006.01)
*A61M 13/00* (2006.01)
(Continued)

(52) U.S. Cl.
CPC ............ *A61M 13/00* (2013.01); *A61B 1/00154* (2013.01); *A61M 13/003* (2013.01);
(Continued)

(58) Field of Classification Search
CPC ... A61M 13/00; A61M 13/003; A61M 16/08; A61M 16/0493; A61M 16/109; A61M 16/1095; A61M 16/161; A61M 16/16; A61M 2210/1067; A61M 2210/0625; A61B 1/000154; A61B 17/3474

USPC ............................ 604/23–24, 26, 93.01, 113; 128/203.16–203.17
See application file for complete search history.

(56) References Cited

U.S. PATENT DOCUMENTS 2,579,113 A  12/1951  Gardner
3,139,088 A   6/1964  Galleher
(Continued)

FOREIGN PATENT DOCUMENTS

GB    2 338 420       12/1999
WO   WO 97/18001      5/1997
WO   WO 98/26826      6/1998

OTHER PUBLICATIONS

Douglas E. Ott, M.D., *Correction of Laparoscopic Insufflation Hypothermia*, Journal of Laparoendoscopic Surgery, vol. 1, No. 4, 183-186 (1991).

(Continued)

*Primary Examiner* — Theodore Stigell
(74) *Attorney, Agent, or Firm* — Knobbe, Martens, Olson & Bear, LLP

(57) ABSTRACT

This invention relates to apparatus used to alter the temperature and humidity of gases. The apparatus of the present invention comprises an insufflator, humidifier and transportation means connected to delivery means to deliver humidified and heated gases to a body cavity prior to and during a medical procedure. In one form of the present invention the insufflator and humidifier are contained in the one housing, while in another form the humidifier is located proximal and external to the insufflator. The transportation means that delivers the humidified gases to the body cavity comprises a flexible tubing having located within, throughout or around it heating means. The heating means may be a heat conductive wire, a ribbon of PTC material, or a conducting wire extruded into the walls of tubing, where the tubing may be made from a PTC material or flexible plastics.

24 Claims, 15 Drawing Sheets

(51) Int. Cl.

| | | |
|---|---|---|
| *A61B 1/00* | (2006.01) | |
| *A61M 16/08* | (2006.01) | |
| *A61M 16/04* | (2006.01) | |
| *A61M 16/10* | (2006.01) | |
| *A61B 17/34* | (2006.01) | |
| *A61M 16/16* | (2006.01) | |

(52) U.S. Cl.
CPC ........... *A61M16/0493* (2014.02); *A61M 16/08* (2013.01); *A61M 16/109* (2014.02); *A61M 16/1095* (2014.02); *A61M 16/161* (2014.02); *A61B 17/3474* (2013.01); *A61M 16/16* (2013.01); *A61M 2210/0625* (2013.01); *A61M 2210/1067* (2013.01)

(56) References Cited

U.S. PATENT DOCUMENTS

| | | | |
|---|---|---|---|
| 3,782,363 | A | 1/1974 | Davis |
| 4,048,992 | A | 9/1977 | Lindemann et al. |
| 4,464,169 | A | 8/1984 | Semm |
| 4,621,633 | A | 11/1986 | Bowles et al. |
| 4,722,334 | A | 2/1988 | Blackmer et al. |
| 4,913,140 | A | 4/1990 | Orec et al. |
| 5,006,109 | A | 4/1991 | Douglas et al. |
| 5,246,419 | A | 9/1993 | Absten |
| 5,411,474 | A | 5/1995 | Ott et al. |
| 5,445,143 | A | 8/1995 | Sims |
| 5,558,084 | A | 9/1996 | Daniell et al. |
| 5,640,951 | A | 6/1997 | Huddart et al. |
| 6,010,118 | A * | 1/2000 | Milewicz ...................... 261/142 |
| 6,068,609 | A * | 5/2000 | Ott et al. .......................... 604/26 |
| 6,078,730 | A | 6/2000 | Huddart et al. |
| 6,349,722 | B1 * | 2/2002 | Gradon et al. ........... 128/203.17 |
| 6,918,389 | B2 | 7/2005 | Seakins et al. |
| 7,120,354 | B2 | 10/2006 | Mackie et al. |
| 7,588,029 | B2 | 9/2009 | Smith et al. |
| 8,206,337 | B2 * | 6/2012 | Blackhurst et al. ............. 604/26 |
| 2004/0149284 | A1 | 8/2004 | Smith et al. |

OTHER PUBLICATIONS

Philippe R. Koninckx & Eugene Vandermeersch, *The persufflator: an insufflation device for laparoscopy and especially for $CO_2$-laser-endoscopic surgery*, Human Reproduction, vol. 6, No. 9, 1288-1290 (1991).

* cited by examiner

APPARATUS USED FOR HUMIDIFICATION OF GASES IN MEDICAL PROCEDURES

CROSS-REFERENCE TO RELATED APPLICATIONS

This application is a continuation application of U.S. application Ser. No. 10/398,099, filed Jul. 1, 2003, now U.S. Pat. No. 8,206,337, which is a national phase filing of PCT Patent Application No. PCT/NZ01/00226, filed Oct. 15, 2001, which claims a priority benefit to New Zealand Application Nos. 507553, filed Oct. 16, 2000, 508850, filed Dec. 12, 2000, and 514314, filed Sep. 19, 2001, each of which is incorporated herein by reference in its entirety.

BACKGROUND

1. Field

This present disclosure relates to altering the temperature and humidity of gases used to inflate body cavities prior to and during medical procedures. More specifically, it relates to apparatus for, and method of, heating, humidifying and filtering insufflation gases prior to passage of the gases into the patient.

Two applications for this apparatus are for laparoscopic and endoscopic procedures, however this application may relate to other procedures which involve the inflation or supply of gas to the patient.

2. Description of the Related Art

Endoscopic procedures are minimally invasive procedures which enable a body cavity to be visualized by inserting surgical instruments through natural openings or small punctures. Endoscopy is used to visualize most areas of the human body such as, gastrointestinal, circulatory, respiratory, auditory, urinary, reproductive, nervous, ocular and musculoskeletal systems.

A body cavity may be visualised by inserting the endoscope through the natural opening, however, some cavities are not able to be entered in this manner due to the cavity being located in the body without a natural opening thus incisions must be made to visualise the cavity. Laparoscopy and thoracoscopy are examples of making small punctures to visualise the body cavity. Upper and lower Gastrointestinal (GI) endoscopy and bronchoscopy are examples of making use of natural orifices to visualise the body cavity.

Most operative laparoscopic procedures begin by creating a viewing and working space inside the peritoneal cavity of a patient to facilitate laparoscopic visualisation and safe, effective instrument manipulation. This intra-abdominal space is typically created and maintained using an insufflator (an adjustable throttling pressure regulator and flow controller), which delivers gas, usually carbon dioxide ($CO_2$) into the peritoneal space, distending the abdominal wall.

There are two ways to introduce gas to the peritoneal cavity. In the first method, an incision may be made in the abdominal wall and a cannula, the instrument through which the abdomen is inflated, is inserted in the incision. In the second method, a needle (for example, a Verres needle) which is attached to a flexible tube connected to an insufflator, is inserted into the peritoneum cavity. Later the needle is withdrawn and a cannula is introduced to the cavity by puncturing the abdominal wall with a trocar. In the second method the abdomen is inflated before insertion of the cannula. In both cases, the tubing from the insufflator is connected to the cannula, and the gas flow from the insufflator is increased to maintain the pneumoperitoneum, the space within the abdomen. After initial insufflation and insertion of a laparoscope through the primary cannula, additional cannulas are placed in the abdomen under laparoscopic observation. At the end of the operating procedure, all instruments and cannulas are removed from the pneumoperitoneum, the gas is expelled, and each incision is closed. For thoracoscopy a similar procedure is followed.

Colonoscopy and sigmoidoscopy are procedures to visualise the lower GI tract by entry into the rectum. Gastroscopy and bronchoscopy are procedures to visualise the upper GI tract and the parts of the lungs through entry into the mouth. These procedures are carried out in similar ways. Most endoscopic procedures begin by creating a viewing and working space inside the body cavity of a patient to facilitate endoscopic visualisation and safe, effective instrument manipulation. The endoscope is inserted into the cavity and visibility is usually assisted by insertion of gas which may be air or $CO_2$. The quantity and flow of gas may be controlled by the clinician performing the examination or by the equipment.

While the importance and use of temperature and moisture conditioning of respiratory gases is known, until recently little attention had been given to the temperature and/or humidity condition of gases used to create a pneumoperitoneum or any other gas filled cavity.

Currently, endoscopic equipment does not heat and humidify the air. An endoscope cable provides both optics and air as well as fluid to the body cavity and thus due to the lack of connections, lack of available space within the cable and the current cable design, it is difficult to heat the fluid and/or air used in these procedures. Usually a cavity is made within the part of the body that is used as a space to manipulate apparatus during the surgery. Dry gas and unheated fluids supplied to the body during an endoscopic procedure can lead to drying of exposed tissue and to the possibility of adverse effects such as cell death and adhesions.

In general, only a small number of insufflators, which are used for surgery in abdominal cavities, are produced today which control the temperature of the gas, and none humidify the gas. When the insufflator provides gas flows of various magnitudes, typically 1 to 10 liters per minute, it must reduce the pressure of the gas from the $CO_2$ cylinder, that being about 57 atmospheres, to approximately 1 atmosphere. Such a process is called "throttling", which causes the gas to be cooled via a thermodynamic process known as Joule Thompson cooling. With $CO_2$ as the insufflation gas, Joule Thompson cooling can reduce the gas temperature as much as 50° C. to 70° C., depending on gas mass flow rates. The large difference in heat capacities of the insufflator metal hardware and the $CO_2$ gas stream permits the gas stream to be reheated to approximately operating room ambient temperature, approximately 20° C., before the gas enters the patient. In the case of large gas flows, this unplanned and uncontrolled reheating effect could be incomplete and the insufflator gas could leave the insufflator apparatus at temperatures considerably less than the ambient temperature of approximately 20° C. In any case, insufflator gas cannot reach a temperature higher than this ambient temperature, and hence, the insufflator gas enters the patient at a temperature substantially less, at least 17° C. less, than the patient's physiological core of approximately 37° C.

Newly developed insufflators and ancillary devices have recognized this problem and have attempted to correct it by adding heat to the gas stream before it enters the delivery system which directs the gas to the cannulas. This method is thermodynamically unsound because it fails to recognize the thermal capacity mismatch between the flowing gas stream and the gas delivery system between the insufflator and the trocar incision point in the cavity even when the delivery system is only 6 to 10 feet of polymer tubing. In addition, this method overlooks the above heat transfer that occurs between the gas stream and the ambient temperature gas delivery tubing. Because of these thermal conditions, the temperature of any gas preheated at or in the insufflator itself will return to approximately the ambient temperature after flowing as little as 4 feet after leaving the insufflator.

U.S. Pat. No. 5,006,109 (Douglas et al.) relocates the temperature sensor to the point of gas administration, but this relocation does not solve this problem, because as has been mentioned above, that point can be, in practice, 6 to 10 feet from any temperature controller. Such an arrangement leads, with the low flow rates typically used in these surgical methods, to "transportation lags" which render stable feedback control difficult to achieve under major rapid flow rate changes which are typically required by these endoscopic and laparoscopic surgical procedures. Thus, the gas reaches the patient at a temperature much lower than the desirable 36° C. to 38° C.

Insufflation gases typically are delivered extremely dry. The extreme lack of moisture in the insufflation gas can lead to drying of exposed surface tissue of the cavity and to the possibility of adhesion formation within the cavity. Also, it was recognised that the lack of moisture could lead to hypothermia.

U.S. Pat. No. 5,411,474 (Ott et al.) discloses an apparatus for treating gas prior to the use of the gas in a medical procedure involving a patient. The gas is received into a humidifier from an insufflator, and the gas exits the humidifier and enters the patient via tubing.

U.S. Pat. No. 6,068,609 (Ott et al.) further discloses an apparatus and method for providing heated and humidified gas to a patient such that heat loss in transfer of the gas is minimized, and such that humidity of the gas is monitored and the temperature of the gas is controlled throughout the procedure.

In both the abovementioned U.S. Patents in the case of laparoscopic procedures the humidifier is connected to the cannula and is thus, proximal to the patient at the trocar incision point in the patient's abdomen. This means the humidifier is within the "operating sterile zone" as the surgeon will be required to touch the humidifier as he/she moves the cannula during the operation to manoeuvre instruments within the abdomen. Therefore, the humidifier must be easily sterilised and capable of maintaining sterilisation.

Furthermore, with the humidifier being located close to the patient, the surgeon may experience obstruction difficulties during the operating procedure that may restrict the movement of the surgeon or instruments in this already crowded space. The surgeon may experience increased fatigue when holding or moving the instruments through the cannula that has the humidifier attached to it. Obstruction difficulties may increase the operation time, and the weight of the humidifier at the incision area may cause bruising and tissue damage, such as tearing, leading to the possibility of increased pain and recovery time of the patient. Furthermore, the humidifier may cause pressure sores or thermal injury proximal to the incision.

SUMMARY

It is therefore an object of the present invention to provide humidifying and related apparatus to heat gases for use with medical procedures which will go at least some way to overcoming the abovementioned disadvantages or to at least provide the industry with a useful choice.

Accordingly, in a first aspect the present invention consists in an apparatus for treating gases prior to the use of said gases in a medical procedure involving a patient, said apparatus comprising or including:

a) an insufflator, which receives gases from a gas source and controls said gases pressure and said gases volumetric flow rate, b) humidification means, located proximal to said gas supply means and distant to said patient and in fluid communication with said gas supply means, c) transportation means in fluid communication with said humidification means, said transportation means having located within, throughout or around it heating means to heat said gases as said gases move through said transportation means, and d) delivery means in fluid communication to said transport means, to deliver said gases to the interior of said patient.

In a second aspect the present invention consists in an apparatus for treating gases prior to the use of said gases in a medical procedure involving a patient, said apparatus comprising or including:

a) an insufflator, which receives gases from a gas source and controls said gases pressure and said gases volumetric flow rate, and b) humidification means, located proximal to said gas supply means and distant to said patient and in fluid communication with said gas supply means, wherein said gas supply means and said humidification means are housed in one housing.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

One preferred form of the present invention will now be described with reference to the accompanying drawings in which.

DETAILED DESCRIPTION

The following description gives but two examples of medical procedures which may use the present invention to heat and humidify gases, by no means is it meant to be limiting. The humidification apparatus and insufflator or integrated insufflating and humidifying apparatus as herein described may be used in many medical procedures for example, endoscopy, laparoscopy, thoracoscopy and upper and lower gastrointestinal endoscopy.

Laparoscopic Procedures

Usually during laparoscopic procedures, to establish a pneumoperitoneum (a cavity filled with gas within the abdomen) the abdominal cavity is punctured by either a needle or using a trocar. If using a needle, the needle is inserted into the inferior portion of the umbilicus and gas from the insufflator used to inflate the abdomen of the patient. The amount of gas used to establish a pneumoperitoneum depends on the size of the abdominal cavity, the development of the abdominal musculature, and the elasticity of the abdominal wall. Three liters of gas is usually sufficient to produce an adequate space in the peritoneal cavity for visualisation. One end of insufflation hose, which is constructed of a flexible plastics material and which ranges in length from approximately 6 to 12 ft, is attached to the insufflator. The other end of the hose is either connected to the insufflation needle or to the cannula inserted in the trocar puncture within the patient's abdomen and the insufflator used to inflate the abdomen. Once the pneumoperitoneum is established, a laparoscope is inserted through the cannula. Additional trocar punctures are often made to provide cannulas for accessory instruments, such as laser probes, biopsy forceps, and irrigators, that can be inserted at other sites in the peritoneal cavity without disturbing the laparoscope. When the procedure is completed, almost all of the insufflating gas is expelled by manually depressing the abdominal wall; any gas remaining in the body cavity will be innocuously absorbed by the body.

Figure 1:
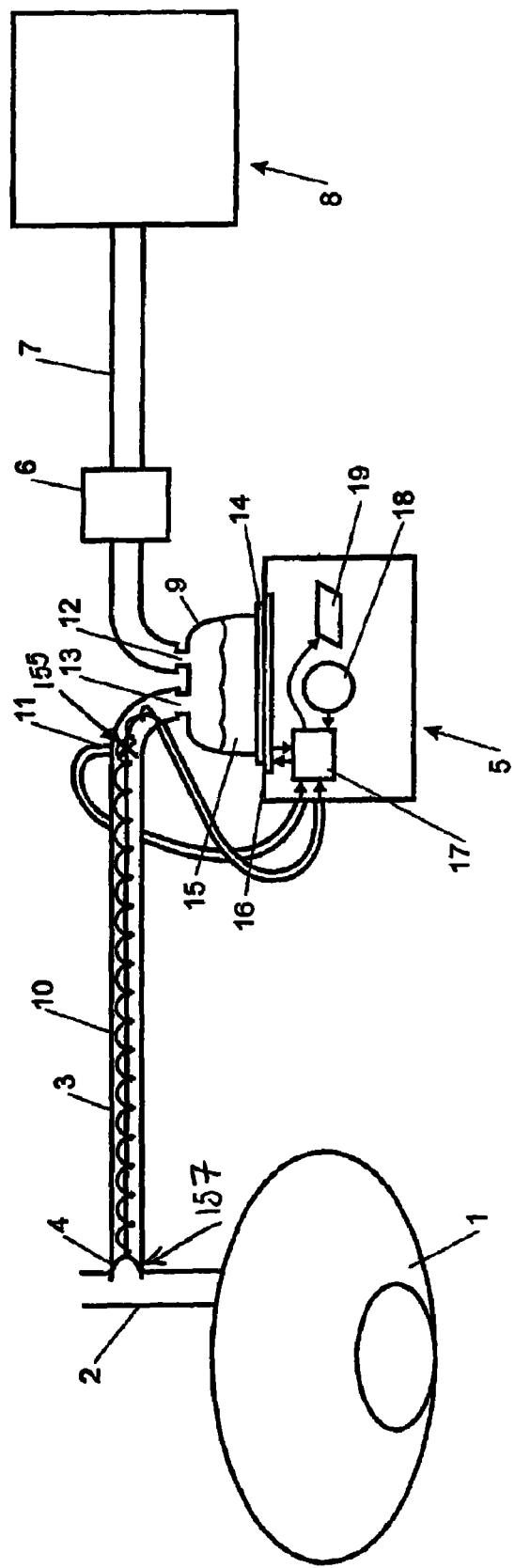
FIG. 1 is a schematic view of the apparatus embodying the present invention, the apparatus being connected to an insufflator at one end and a means for delivering gas to a patient, namely at a cannula, at the other end.

Referring now to FIG. 1, when using the apparatus of the present invention during a laparoscopic procedure, the patient 1 has inserted within it's abdomen a cannula 2, as previously described, which is connected to a flexible conduit 3 preferably via a Luer lock connector 4. The flexible conduit 3 is preferably made of a flexible plastic and is connected to a humidifier 5. The humidifier 5 is preferably in serial connection to a filter 6, which is connected to an insufflator 8 via a further conduit 7, also preferably made of flexible plastic tubing.

The insufflator 8 preferably provides $CO_2$ gas to the filter 6, the gas is then filtered and passed via conduit 7 to the inlet 12 of the humidifier 5. The gas is humidified as it is passed through a humidifying chamber 9, which is effectively a water bath, and the gas flows out through the humidifier's outlet 13 and into the conduit 3. The gas then moves through the conduit 3 and into the patient 1 via the cannula 2, thereby inflating and maintaining the pressure within the patient's abdomen.

The humidifier that can be used in the preferred embodiment of the present invention may be a humidifier as manufactured by Fisher & Paykel Limited, or a humidifier as disclosed in U.S. Pat. No. 5,558,084 (Fisher & Paykel Limited), or any other equivalent or similar device.

Alternatively, the humidifier as used in the preferred embodiment of the present invention may be of the type described below with reference to FIGS. 1 and 2. The humidifier 5 has a humidification chamber 9 that comprises a plastic formed chamber having a metal base 14 sealed thereto. The humidification chamber 9 is adapted to hold a volume of water 15, which is heated by a heater plate 16, which is under the control of a controller or control means 17 of the humidifier. As the water 15 within chamber 9 is heated it slowly evaporates, mixing water vapour with the gases flowing through the humidification chamber 9 from the filter 6 and insufflator 8. Accordingly, the humidified gases leave the humidification chamber 9 via outlet 13 and are passed to the patient 1 via conduit 3.

The humidifier comprises a body 20 containing heating means comprising a heating plate 16 having an electric heating element therein or in thermal contact therewith and control means 17, for example, electronic circuitry which may include a microprocessor for controlling the supply of energy to the heating element. The body 20 is removably engageable with a humidifying chamber 9.

The gases to be humidified are supplied to the chamber 9 through a gas inlet 12. The gas outlet 13 is provided and is connected to the conduit 3, which conveys the humidified gases to the patient. The humidifier heater plate 16 preferably has a temperature transducer, which is in electrical connection with the electronic control circuitry in body 20 of the apparatus so that the control means monitors the temperature of the heating plate and the approximate temperature of the humidified gases at the gases outlet 13.

The humidifier may also be provided with a temperature sensor 11 that monitors the temperature of the humidified gas leaving the humidifier 5 from outlet 13, and if necessary increases the temperature of the gas to that temperature required by the patient, namely 37° C., this being the physiological temperature of the human body.

The temperature and flow probe 11 is connected to the control circuitry in the body 20 via socket connector 22. Additional sensors may be incorporated, for example, for sensing at the patient end of the conduit 3.

Preferably, gases leaving the outlet 13 of the humidification chamber 9 will have a relative humidity of around 100% and that as the gases travel along conduit 3 there is a chance that water vapour may condense on the conduit wall, detrimentally reducing the water content of the gases. It is preferable that the water content of the humidified gases supplied to the patient is as high as possible. In order to minimise the occurrence of condensation within the conduit 3, a heater wire 10 may be provided within throughout or around the conduit. The heater wire 10 is preferably an insulated copper alloy resistance wire wound around an insulating core, but may be made of any other appropriate material. Power is supplied to the heater wires from the humidifier 5 via connection 21 which plug into sockets in a plug or connection at the end of the conduit 3. The heating wire 10 is preferably energised under the control of control means 17 housed in the humidifier body 20. Preferably the insulating coating around the heater wire is a thermoplastics material which, when heated to a predetermined temperature, enters a state in which its shape may be altered and the new shape substantially elastically retained upon cooling.

The heater wire 10 may be wound in a single or double helix and is designed to ensure the conduit surface temperature does not exceed 44° C. and/or to ensure the gas temperature delivered to the patient does not exceed 43° C.

The heating wire 10 provided within the conduit 3 has an additional function of maintaining the temperature of the gas flowing through the conduit 3 between approximately 35° C. and 45° C., but the wire can also provide additional heating of the gas to elevate the gases temperature to maintain the humidity generated by the heated water bath in the humidifier. Due to the unheated cannula the gas cools, and the gas entering the body cavity is a few degrees cooler than the gas was in the conduit 3 and it is fully saturated. Therefore, the heater wire 10 maintains and heats the gases in the conduit 3 and prevents condensation (due to the conduit being exposed to the air temperature) of the humidified gases within the conduit. As shown in FIG. 2, the heater wire 10 is connected to the tubing 3 via various connectors, which are in turn connected to the control circuitry in the body 20 of the humidifier via a socket connector 21.

Control means 17 may, for example, comprise a microprocessor or logic circuit with associated memory or storage means which holds a software program which, when executed by the control means 17, controls the operation of the humidification system in accordance with instructions set in the software and also in response to external inputs. For example, the control means may be provided with input from the heater plate 15 so that the control means is provided with information on the temperature and/or power usage of the heater plate. In addition, the control means could be provided with inputs of temperature of the gases flow, for example a temperature sensing means or temperature probe 11 may be provided to indicate to the control means the temperature of the humidified gases flow as it leaves the outlet 13 of the humidification chamber 9. Furthermore, a flow sensing means or flow probe may be provided in the same position as the temperature probe or at any other appropriate position.

A still further input to the control means may be a patient input means or switch 18 which could be used to allow a patient, such as a surgeon or nurse, to set a desired gas temperature or gas humidity level to be delivered. Alternatively other functions could be controlled by switch 18 such as control of the heating delivered by a heater wire 10.

A further feature of the humidification apparatus may be the incorporation of the display means 19 for displaying to the patient the gases temperature being supplied to the patient 1.

Figure 2:
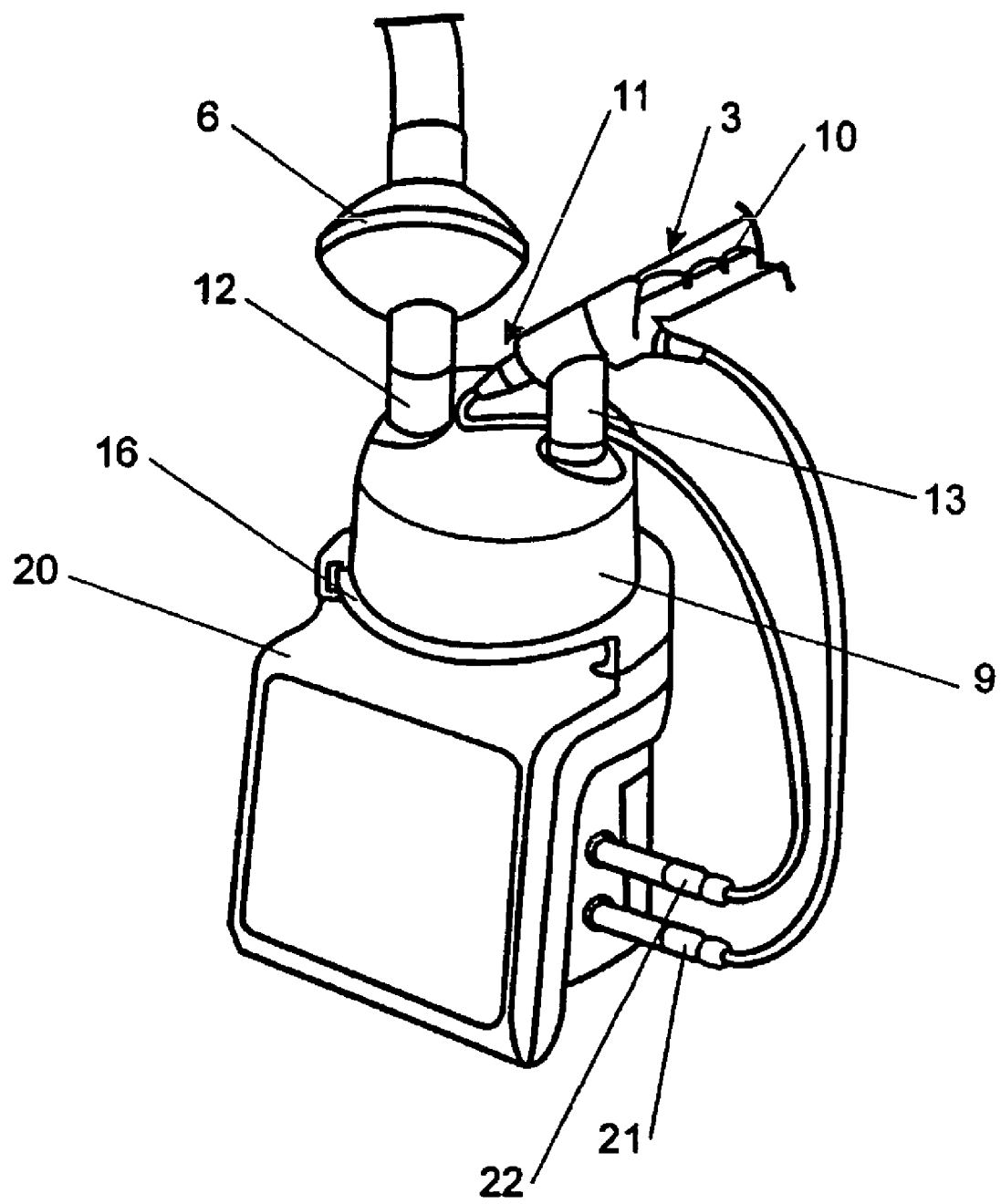
FIG. 2 is a more detailed perspective view of the humidifier that may be used in the apparatus of the present invention.

Referring to FIG. 2, the filter 6 of the present invention is preferably injection moulded from a medical grade polypropylene material and is preferably located and attached to the inlet 12 of the humidifier. The filter media may be varied according to the intended application to include, for example antimicrobial properties or simply to be a particle filter. In this latter role the filter material may, for example, be a non-woven felt of electrostatically charged fibres, such as that marketed under the trademark ELECTROSTAT™ by All Felt Incorporated. Alternative examples of appropriate filter media may be paper media, which may be pleated and/or coated. In particular, the filter must be able to filter particles and pathogens from the gas stream and it must comply with appropriate medical standards.

The placement of the filter 6 at the inlet 12 of the humidifier 5 has the purpose of preventing contaminated gases reaching the patient. Also this placement enables the filter to protect the insufflator from any reflux from the patient that may flow through the humidifier. Alternatively, the filter may be located at the outlet of the humidifying chamber.

Integrated Insufflating and Humidifying Apparatus

Figure 3:
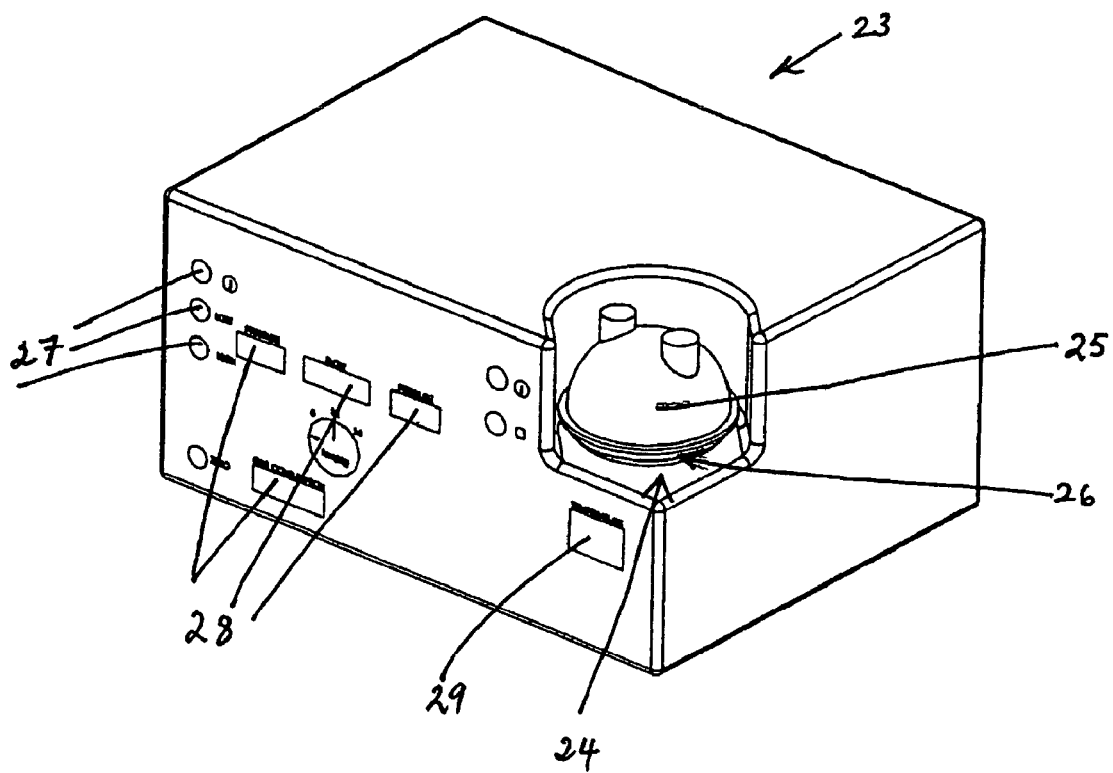
FIG. 3 is a perspective view of an alternative embodiment of the present invention, wherein an insufflator and humidifier are contained within an enclosure.

In an alternative form of the present invention the humidifier is included in the same housing as the insufflator apparatus. Referring to FIG. 3, a drawing of the insufflator with humidifier of the present invention is shown. Firstly, an insufflator is a machine that regulates or delivers gas from a high pressure gas source, such as a gas cylinder or a gas outlet provided in a wall or the like, where the gas source can be readily connected to the outlet, to a gas delivery tube, where the gas pressure and flow rate is controlled based on pressure fed back from the distal end of the tube delivering gas to a patient.

As shown in FIG. 3, in the alternative embodiment the insufflator and humidifier are preferably housed within an enclosure 23. The enclosure 23 is preferably rectangular in shape and made of a sheet metal or an appropriate plastic type material.

The enclosure 23 has a recess 24 that provides an area for a humidifying chamber 25 to be located in. The chamber 25 is situated upon a heater plate 26, which is connected to electronics that heat the plate 21, and enables humidification of the gas within the chamber when the chamber has water placed within it. The recess 24 is preferably located at the top right corner of the rectangular enclosure 23. The enclosure 23 may be provided with any number of dials 27 that allow an operator to alter the temperature, pressure and flow of the gas moving through the enclosure 23. Furthermore, the enclosure 23 may be provided with any number of displays 28 showing various gas states such as temperature, pressure and flow rate. The enclosure 23 is also preferably provided with a display relating to the humidifier, which may indicate the temperature and/or humidity of the gas exiting the chamber 25.

Figure 4:
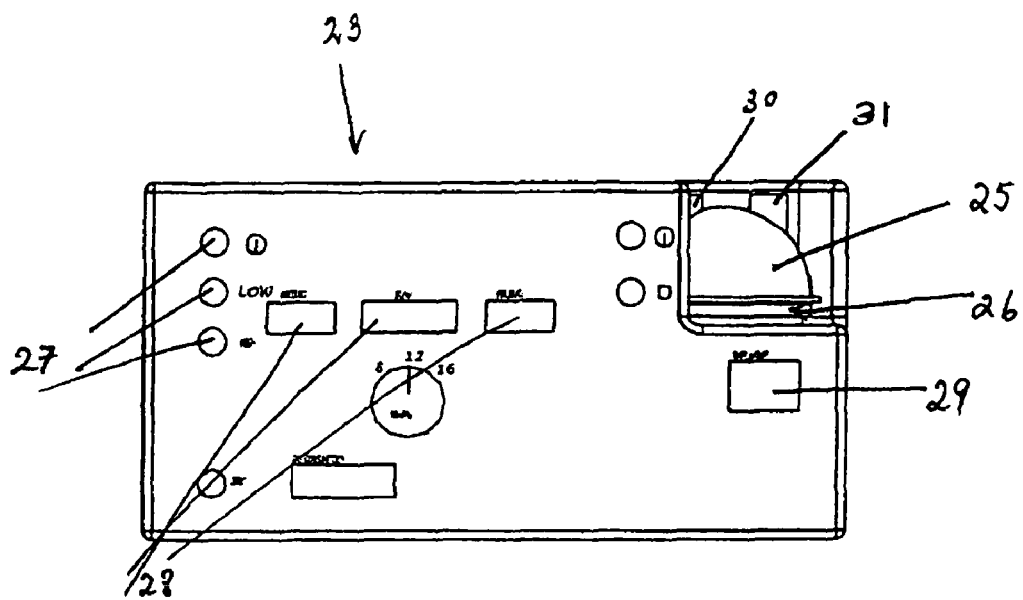
FIG. 4 is a front view of the alternative embodiment of the present invention as shown in FIG. 3.
Figure 5:
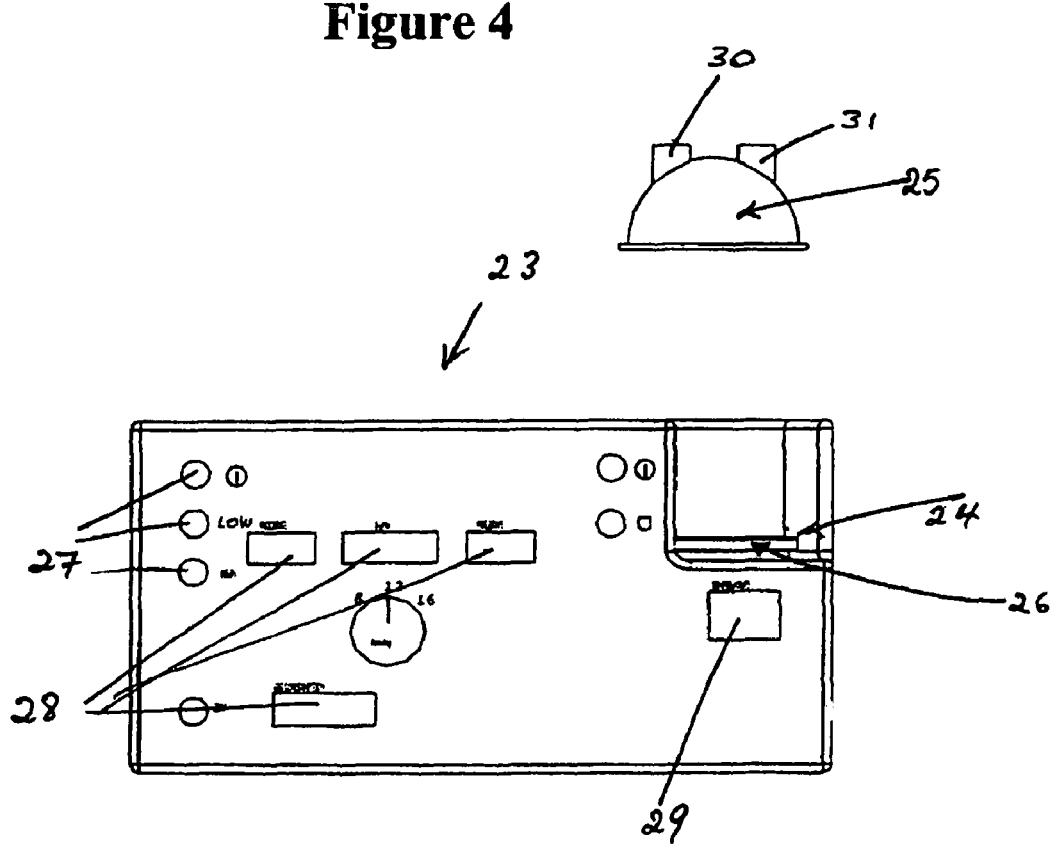
FIG. 5 is a front view of the apparatus showing the humidifying chamber removed from the enclosure and heater plate.

Referring now to FIGS. 4 and 5, the chamber 25 has an entry port 30 that is connected to the outlet of the insufflating machine housed within the enclosure 23, and an exit port 31 that has connected to it a polymer tube (see FIG. 6) that carries the gas to the patient. As described previously the chamber 25 may be partially filled with water by pouring water into one of the entry or exit ports. Alternatively, the chamber may have an auto feed mechanism as described in U.S. Pat. No. 4,913,140 or U.S. Pat. No. 5,445,143 (Fisher & Paykel Limited). FIG. 4 shows the chamber 25 sitting upon the heater plate 24 within the recess 24 within the enclosure 23 whereas FIG. 5 shows that the chamber 25 can be removed from the heating plate 26 in order to allow for cleaning of the chamber 25 and/or heater plate 26 or replacement of the chamber 25.

Figure 6:
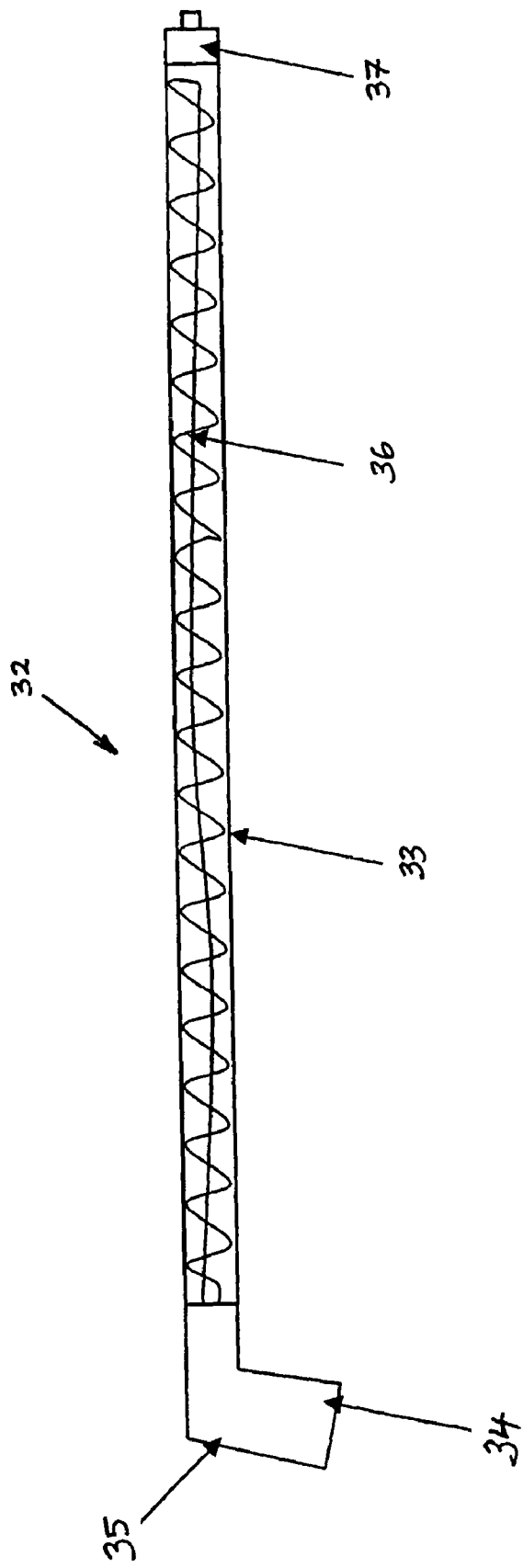
FIG. 6 is a side view of the heated gas delivery system, wherein a polymer tube carries gas to the patient.

External to the enclosure is a heated gas delivery system, which is shown in FIG. 6. This takes warm humid gas from the enclosure and delivers it to the patient, maintaining temperature and humidity of the gas. The delivery system 32 comprises a polymer tube 33, connectors, an electrical socket and spiral wire. Preferably the tube 33 is made of a suitable material, for example, a plastic type material that has such properties that enables the material to maintain dimensional stability and not melt. The enclosure end of the tube has a connector 34 suitable for connecting to the gas outlet of the humidifier and an electrical socket 35 suitable for connecting to the electrical outlet of the humidifier (not shown) within the enclosure 23. Within the tube 33 is a spiral wound heater wire 36, such as that described in U.S. Pat. No. 5,640,951 or U.S. Pat. No. 6,078,730 (Fisher & Paykel Limited) running inside part of, or all of the length of the tube 33. The terminations of this heater wire are connected to the electrical socket 35 of the enclosure end connector 34. Finally, the patient end of the tube 33 has a standard 6% taper male Luer lock connector 37, which is connected to the cannular inserted in the patient's body cavity.

Figure 7:
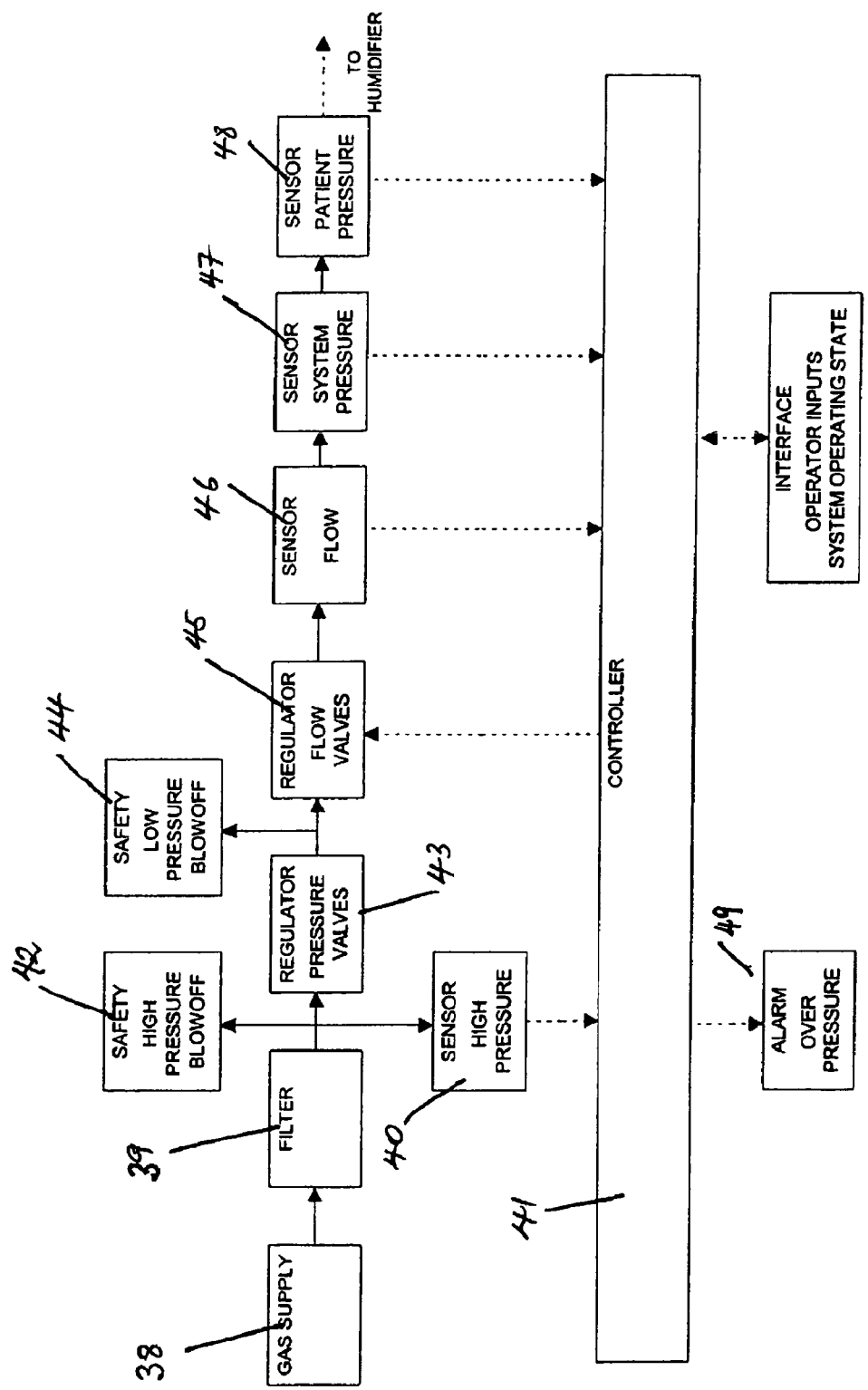
FIG. 7 is a schematic view of the insufflator of the present invention.

Referring now to FIGS. 3 and 7, the insufflator, housed within an enclosure 23, comprises a standard gas cylinder connector located in one side of the enclosure 23, for connecting the high-pressure gas supply 38 to the inlet of the insufflator. Preferably a filter 39 is provided which filters the gas at the entry to the insufflator apparatus. As gas moves through the insufflator apparatus preferably through a series of tubes or pipes, the gas passes a pressure sensor or sensors 40. The outlet of the sensor(s) 40 is fed back to a controller 41 and a high-pressure blow off valve 42 acts as a safety valve that releases gas from the apparatus in the event that the pressure from the gas cylinder is too high. The blow off valve therefore protects the internal elements of the apparatus from high gas pressure damage. Next, the gas moves through any number of pressure regulators 43 which reduce the pressure of the gas to a level which is safe for use in endoscopic procedures or the like. Then the gas passes a low-pressure blow off valve 44, which again allows the gas to be released from the apparatus. The gas then moves through any number of flow regulators 45 which ensure the flow rate is at a safe to use level.

The combination of valves as already described receiving the low pressure gas are actuated by signals from the controller 41. Following the valves are flow sensors 46 and pressure sensors 47 and 48, which provides feedback to the controller 41. The flow and pressure sensors are preferably located within the insufflator enclosure 23. The insufflator may also be provided with various operator interface controls such as on, off, insufflation pressure and flow rate inputs, which may be entered and set by an operator, these are shown as dials 27. The operator interface may also provide a visual output viewable by the operator of the system which shows system operating states such as gas supply pressure, flow rate through the insufflator, gas consumption, system pressure, patient pressure, input settings or other appropriate operating states, shown on FIG. 3 as displays 28 and 29. Therefore, the controller 41 is able to utilise operator inputs, gas pressure and flow inputs to switch the flow valves 45 as required. The controller 41 also has the capability of monitoring pressure and provides output to an audible alarm 49 and dump valves, such as a high pressure blow off valve 40, warning an operator if gas pressures are too high.

Figure 8:
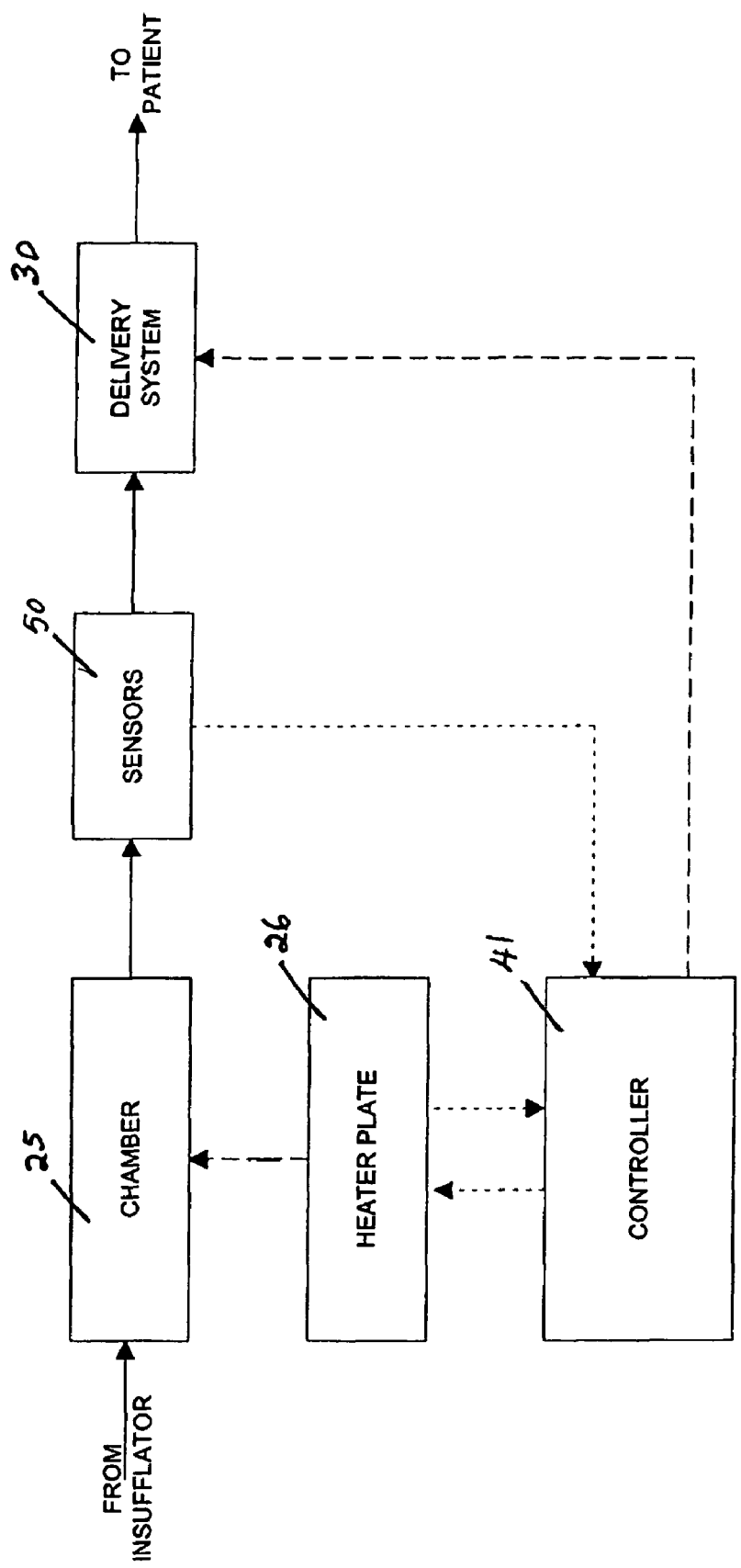
FIG. 8 is a schematic view of the humidifier of the present invention, in particular showing the humidifier's main components.

Referring now to FIGS. 3, 6 and 8, the humidifier housed within the enclosure 23 is shown in schematic form in FIG. 8. The gas moving through the tubing within the enclosure 23, after passing various regulator flow valves and sensors, flows into the chamber 25 that heats and humidifies the gas. The chamber 25, which comprises a plastic formed chamber having a metal base sealed thereto, has the base of the chamber positioned on a heater plate 26 that heats the chamber base to allow heating and evaporation of the water within the chamber. The chamber 25 is preferably able to be detached from the heater plate 26 to enable cleaning of the heater plate and/or replacement of the chamber. The heater plate 26 is connected via standard electrical connections to the controller 39. Furthermore, the controller 41 has a connection such as an electrical output to the external heater wire 34 that resides in the delivery tube 30 that delivers the output gas to the patient. When gas leaves the chamber 25 through an outlet port flow, temperature and/or humidity sensors 50 may be positioned within the heated tubing 32 in the gas stream to provide the operator with various indications as to the state of the gas. The controller 41 may also receive temperature input from the heater plate 26 and temperature, flow and/or humidity inputs from the sensors 50. These inputs may be used to produce an output for controlling the heater and the electrical output to the heater wire 36 on or off.

In prior art devices the heating and humidifying of the $CO_2$ before entering the patient's abdomen assists in maintaining the core temperature of the patient. The heating and humidifying of the $CO_2$ also minimises evaporative loss of fluid of the peritoneum by delivering saturated body temperature $CO_2$ to the peritoneum. Furthermore, it has been found that with the addition of heating and humidifying the $CO_2$ the patient will experience less post operative pain and will be able to return to normal activities and work within a shorter time period.

The humidifying apparatus of the present invention has various advantages over the prior art. Firstly, with the humidity source being at the insufflator end rather than at the patient end means that the humidity source is not in the surgeon's way and does not restrict movement during the operation. Also less weight is added to the cannula and the power source is distant from the patient.

Also, the humidifier is used in conjunction with a heating element; this is to prevent heat and humidity loss over the conduit, which allows the humidifier to be located away from the patient. The humidification and heating of the gas allows the gas to be provided to the patient at more physiologically correct levels than previously, which provides further benefits to the patient. Furthermore, less condensation within the conduit between the humidifier and patient occurs, therefore meaning that there is less chance of occlusion and hence less chance of low or high-pressure effects. These effects being, if a pool of water was established within the conduit the pressure recorded at the insufflator would vary due to restriction of the gas movement through the tube. As the insufflator is reading incorrect pressure then the pressure within the peritoneum cavity is likely to be unstable.

In the preferred form of the present invention the humidifier and filter are not in the same housing, this prevents contact of water with the filter and thus water pressure "burst through" issues within the filter are eliminated. Also, if the filter is positioned upstream of the humidifier, it remains dry and the filter only filters gas rather than liquids.

The separate water bath of the humidifier acts as a reservoir or buffer for any fluid that may travel from the patient through the tubing to the humidifier and possibly to the insufflator. Therefore, the possibility of liquid contamination into the insufflator is greatly reduced.

Endoscopic Procedures

When referring to insufflating and humidification system herein reference is being made to either the integrated insufflator and humidifier or the system that has a separate insufflator and humidifier.

With the other types of equipment such as colonoscopes whereby the optics, gas and water functions are all integrated, the application of humidity to the gas would require a gas source such as an insufflator. To supply humidified and pressurised air to a body cavity in such an endoscopic procedure an interface is required between the cavity opening and the tubing (endoscope) supplying optics, gas and water to the body cavity.

Figure 9:
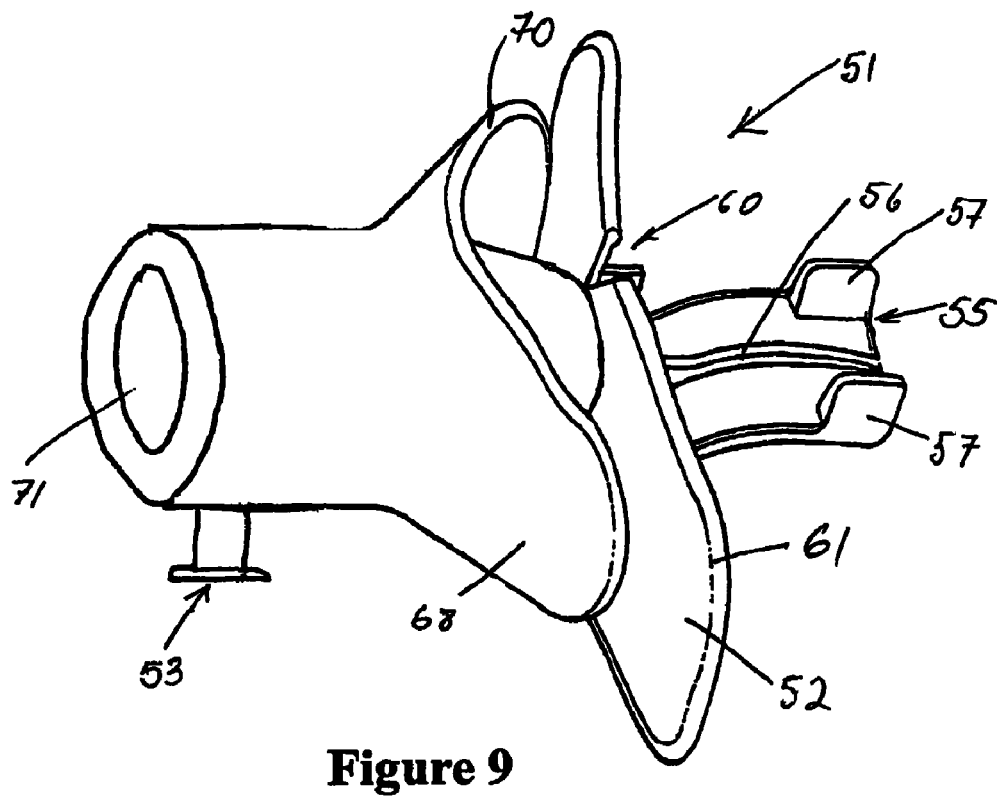
FIG. 9 is a perspective view of the oral interface that may be used with upper endoscopic procedures that is locatable within patient's mouth with the outer flap in place.
Figure 10:
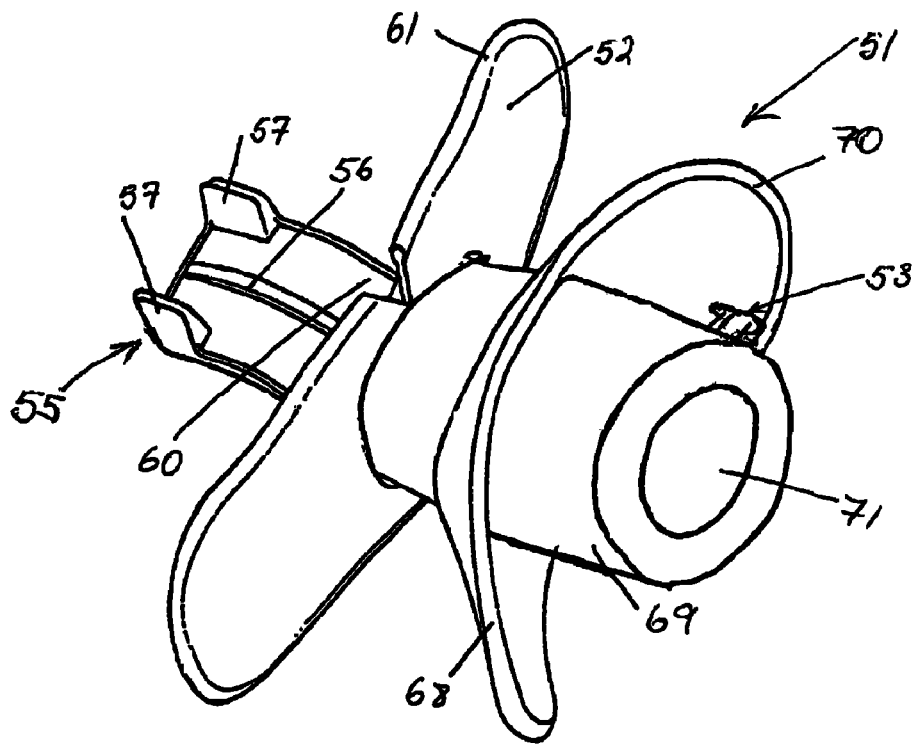
FIG. 10 is a perspective view of the oral interface with the outer flap bent back in a position that allows easy insertion.
Figure 11:
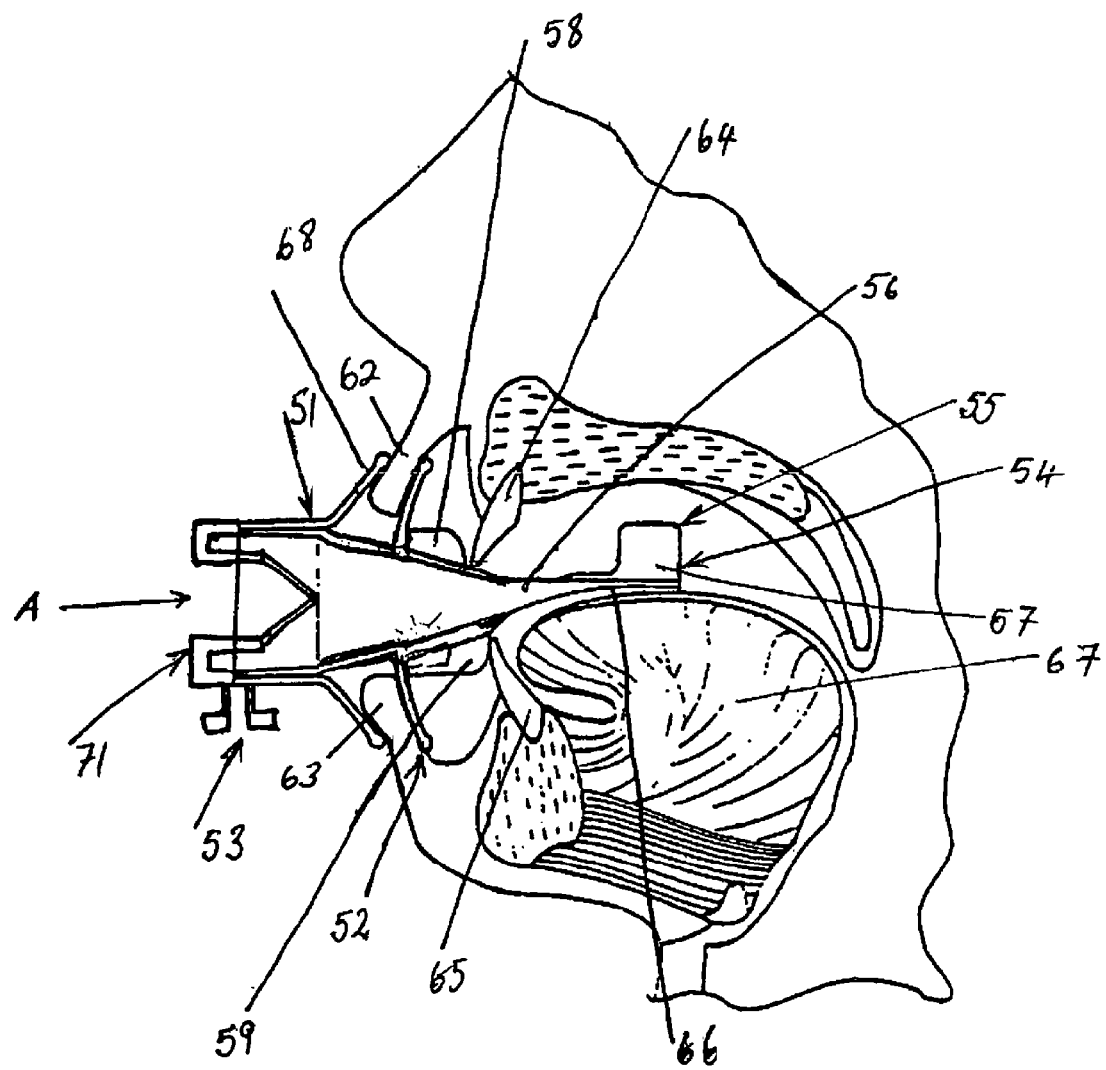
FIG. 11 is a cut-away view of the oral interface and its use with a patient.

For upper GI endoscopy the interface may be in the form of an oral interface, as shown in FIGS. 9, 10 and 11. Such an interface enables the heated gas to be channelled into the body cavity, in this example, the stomach, but also allows the flexible endoscope to enter the body cavity yet still allow for easy manipulation of the endoscope.

Referring to FIG. 9, the oral interface acts as an interface between the patient and the insufflating and humidification system as shown in FIG. 2, to supply humidified, pressurised gas to the body cavity. The anatomy of the mouth of the patient is used to ensure the oral interface 51 remains in place. The oral interface 52 includes a vestibular shield 52 being a generally flat and generally rectangularly shaped member in front elevation having a curved profile that reflects the curvature of a patient's jaw and in turn the curvature of the labial vestibule region. A gases passageway stems through the vestibular shield from an inlet 53 at the Luer connector 53, located on the part of the interface that is external to the patient the lure connector providing the connection to the conduit 3 (as shown on the system of FIG. 1) and receives gas flow from the insufflating and humidification system. A gaseous passageway extends through the vestibular shield from the inlet at the Luer connector 53 to an outlet 54 (as shown on FIG. 11). The oral interface 51 includes a tongue depressor 55 extending from the inner space of the vestibular shield 52. The tongue depressor includes a vertical stiffening flange 56 centrally located on its upper surface and extending from the gases outlet 54. In use, gases flow easily around the stiffening flange 56 effectively bifurcating the gaseous outlet 54. The tongue depressor 55 further includes a pair of vertically extending spaces 57, which in use, may abut against the roof of the patient's mouth and ensure that the tongue cannot completely block the air passage way. In the oral interface 51 the sealing effect of the vestibular shield 52 against the lips of the patient is enhanced by providing teeth abutments 58 and 59 (as shown in FIG. 11). In particular, an upper teeth abutment 58 and a lower teeth abutment 59 are provided, with the lower teeth abutment 59 protruding further from the inner face of the vestibular shield 52 than the upper teeth abutment 58. This difference serves to match the typical over bite of most patients. The abutments 58 and 59 are not required to be wider than the gases outlet 52. A notch 60 is provided centrally in the upper edge of the vestibular shield 52 to accommodate the upper frenal attachment. A slight bead 61 is provided around the edge of the vestibular shield 52 for patient comfort, with the vestibular shield 52 otherwise being very thin for additional suppleness. The vertically extending spaces 57 are of a soft and supplement material, as are the upper and lower teeth abutments 58 and 59.

The oral interface 52 has an extra oral sealing flap 68. The flap 68 in its natural bias is tapered, the wide-open end of which is shaped to conform to the facial contours around the outside of the patient's mouth. The narrow end joins to a cylindrical section, which is designed to slide over the endoscope inlet portion 69. While this is one method of attachment the flap 68 might also be constructed as an integral part of the interface 52. The flap 68 needs to be constructed on a flexible material such as silicone rubber can be employed to fashion the flap. The outer flap 68 as seen in FIG. 10 in a bent back position. It will be appreciated that when the oral interface 52 is being inserted into the mouth of the patient, the outer flap 68 is intended to be in this bent back position to aid insertion. Prior to insertion, the outer flap is bent back by simply pressing on its outer periphery 70, until its snaps into the bent back position, in which it will stay unaided.

Referring now to FIG. 11, use of the oral interface 52 according to FIGS. 9 and 10 is depicted. The upper and lower lips 62 and 63 are further distended by the abutment action of the teeth abutments 58 and 59 against the upper and lower teeth 64 and 65 respectively, thus forming a seal of greater pressure between the lips 62 and 63 and the upper and lower portions respectively of the vestibular shield 52. A lower face 66 of the tongue depressor 55 impinges if necessary on the upper surface of the tongue 67 and retains the tongue in the lower portion of the patient's mouth. This ensures a clear gases outlet 54 from the gases passageway through the vestibular shield. The vertically extending spaces 57, if forced by pressure from the tongue, will engage against the roof of the patient's mouth and maintain a clear air passageway. This stops the anaesthetic patient unconsciously blocking the oral passageway and reverting to nasal breathing.

In FIG. 11 also illustrates the outer flap 68 in use in the mouth of a patient. Once correctly positioned in the mouth, the outer flap 68 may be adjusted into its operational position by pressing on the outer periphery 106 until it snaps back to the press against the outside of the mouth. Due to the relative position of the vestibular shield 52 and the outer flap 68, the outer flap 68 is unable to fully reach its natural bias and thereby inflicts a compressive force on the outside of the patient's mouth.

It will be appreciated that as well as providing a substantially air tight seal the additional outer flap provides enough compressor force on the mouth to keep the oral interface in place without the need for straps.

This oral interface when used with the present invention does not require custom orthodontic fitting as it does not rely on accurate alignment with the patient's teeth or palate to provide location and retention within the patient's mouth, but instead resides in the vestibular between the teeth and lips and the teeth and cheeks, and the lateral and vertical extension of the vestibular shield requires that the patient's lips be actively manipulated for the vestibular shield to be removed. With the addition of the extra oral flap, the oral interface and associated tubing, connected to the Luer connector, is held securely in place without the need for external strapping, and an effective seal is created around the patient's mouth.

In use with the insufflating and humidifying system of the present invention an endo scope may be inserted in the direction of arrow A in FIG. 11. The tube extends through the interface 51 and tongue depressor 55 into the stomach of the patient. The endoscope is held, but easily manipulated within the interface, by a valve 71.

Figure 12:
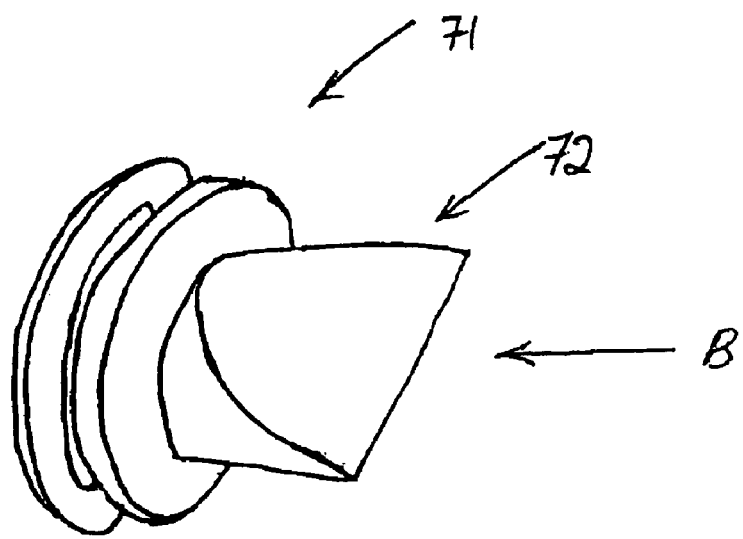
FIG. 12 is a perspective view of the valve used with the oral interface in the open position.

The valve 71 that receives the endoscopic tube will now be described with reference to FIGS. 12 and 13. The valve 71 is manufactured in a silicone grade material and has a circular profile that allows it to fit within the inlet to the oral interface.

Figure 13:
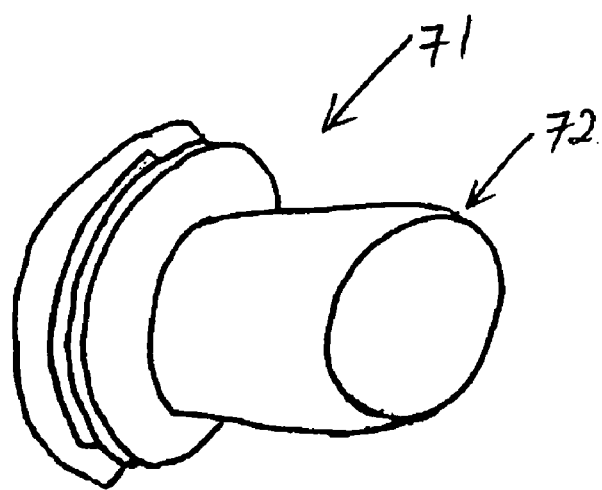
FIG. 13 is a perspective view of the valve used with the oral interface in the closed position.

In use, when an endoscope is inserted through the insertion end 72 the valve opens as shown in FIG. 13. Here the valve 71 is of the type having a silicone diaphragm with an aperture. The aperture in the silicon diaphragm can be pushed open when inserting an endoscope into the aperture, but which retains a seal around the endoscope, thereby retaining the pressure within the body cavity. If the endoscope is retracted from the valve as the end of the endoscope is drawn through the aperture the silicon diaphragm again maintains a seal around the endoscope and the aperture closes slowly closes around the end of the endoscope to be fully closed once the endoscope is fully removed from the valve. The valve in the closed position is shown in FIG. 12. Thus the valve prevents loss of pressure within the body cavity when the endoscope is removed.

Figure 14:
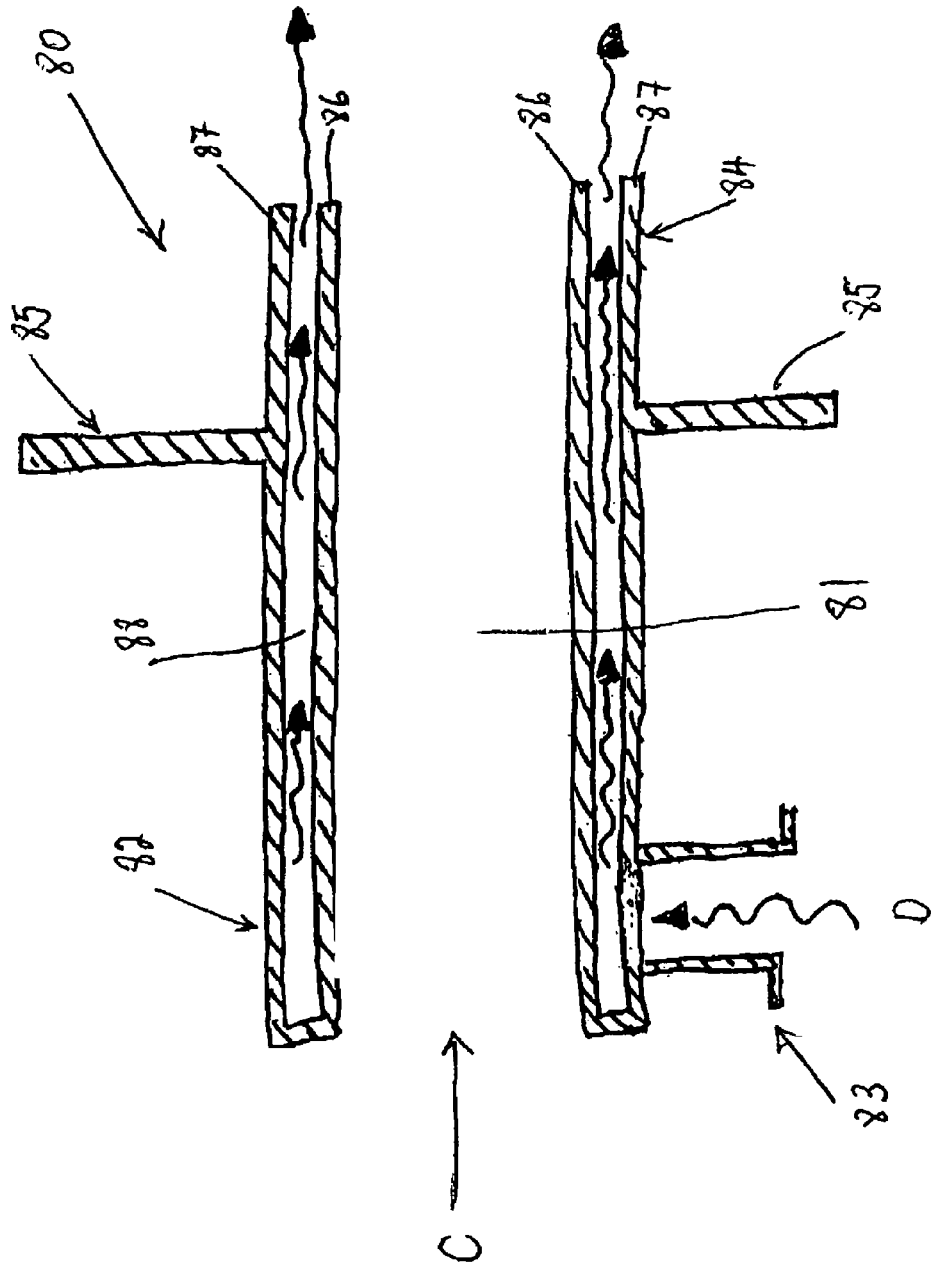
FIG. 14 is a cross-sectional view of the rectal interface that may be used for lower GI endoscopic procedures.

Referring now to FIG. 14, for lower GI endoscopy an interface 80 similar to the oral interface may be used. However, the interface 80 is inserted in the patient's anus rather than the mouth. This rectal interface 80, due to the anatomy of the anus, is a tubular device having a passage 81 through which a flexible endoscope may be inserted through (in the direction of arrow C). The end 82 remains external to the patient and is provided with a connector, such as a Luer connector 82 that is connected to the conduit 3 (of FIG. 1) to provide humidified and pressurised gas to the body cavity. The other end 84 of the rectal interface 80 is inserted in the anus of the patient and held there by the action of the anus muscles. The flange 85, located partially along the length of the tubular interface extends outwardly from the interface and provides a stop to prevent over insertion of the interface within the anus. The rectal interface 80 has an internal wall 86 and external wall 87 which provide an interior passage 88 in which gases flow after entering through the Luer connector 83.

In use, the end 84 of the rectal interface is inserted into the anus of a patient up to the flange 85 and humidified and pressurised gas enters through the Luer connector 83, in the direction of arrow D, into the interior passage 88 provided in the interface 80 and exits through the passage 88 at the end of the interface that has been inserted in the anus. Thus humidified gas has been provided to the body cavity along with pressure, which inflates the body cavity, without hindering the manipulation of the endoscope within the body cavity. In fact, the maintaining of inflation (pressure) within the cavity helps to prevent discomfort associated with over pressure and assists with the manipulation and use of the endoscope.

The rectal interface 80 may be provided with a valve 71 (as described above with reference to FIGS. 11, 12 and 13) across the inlet to the passage 81.

PTC Tubing

To overcome the disadvantages associated with temperature sensors, for example, having a temperature sensor at the point of gas administration where transportation lags occur causing condensation in the delivery tube, the insufflating and humidifying system of the present invention may include removing the need for a sensor at the patient airway. To remove this sensor safely, there must be a certainty that the gas entering the delivery tube has a safe level of temperature and absolute humidity, and that the surfaces inside the delivery tube do not exceed safe temperature levels. This implies a delivery tube that has a constant internal wall temperature.

It would be desirable, therefore, to have a heated delivery tube which self-regulates its temperature at a desired level. The conduit 3 as described with reference to FIG. 1 consists of a flexible tube containing a heater. The gas from the insufflating and humidifying system passes through the tube and is heated by the heater to offset heat losses through the walls of tube. In this further alternate form of the present invention the conduit itself is a heated delivery tube which self-regulates its temperature at a desired level. The heater may be embedded in the wall of the delivery tube itself, form the fabric of the tube or lie inside the lumen of the delivery tube. The heater of the present invention is formed from a positive temperature coefficient (PTC) material.

The resistance of PTC material increases markedly once it reaches a threshold temperature, resulting in reduced power consumption and subsequent cooling. The delivery tube may pass through more than one environment, or may have localised drafts present on certain parts of the tube.

Figure 15:
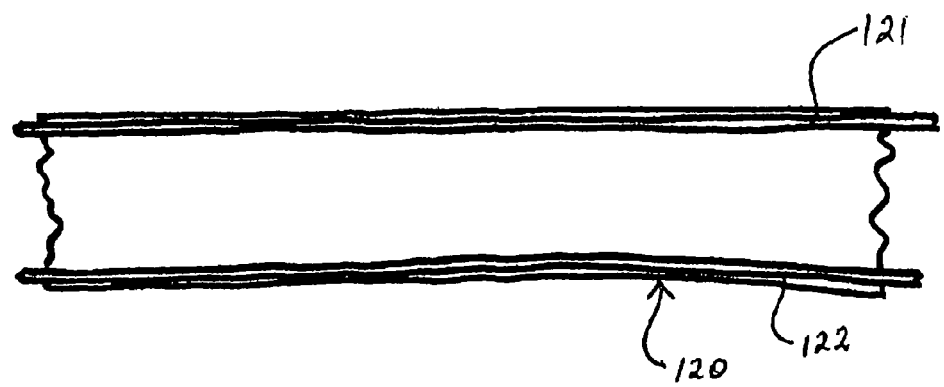
FIG. 15 is a plan view of a section of a ribbon of PTC material with an electrode embedded along each edge.

In one embodiment of the present invention the PTC heater is provided as an elongate structure lying within the lumen of the delivery tube. The construction according to a preferred embodiment is illustrated with respect to FIGS. 15 to 17. In particular the heater structure is formed from a ribbon 120 of PTC plastic material with conductors 121, 122 embedded in the plastic material adjacent the opposite edges thereof. In use the conductors are attached to a power supply to provide a voltage difference between the conductors and cause a current to flow between them depending on the resistance of the PTC material.

Figure 16:
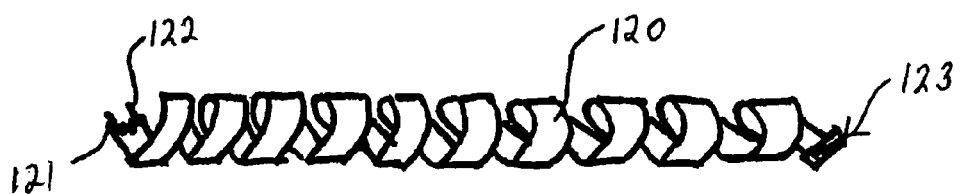
FIG. 16 is a plan view of a spirally configured heater element using the PTC ribbon of FIG. 15.
Figure 17:
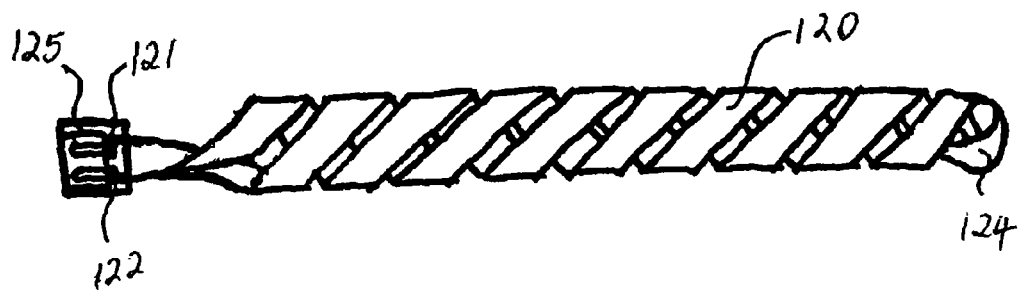
FIG. 17 is a plan view of a second form of spirally configured PTC ribbon heater element.

The ribbon may be provided in the tube as a single length of ribbon blindly terminated at one end and terminated with a power connector at the other end. This configuration is illustrated in FIG. 16 where the ribbon 120 is wound into a generally helical configuration and is terminated at one end with a blind connector 123. Termination of the other end at a power connector is not shown. In a alternative configuration the ribbon may be provided as a loop so that both ends terminate at the power connector with both ends of the positive electrode terminating at the positive pin and both ends of the negative or ground electrode terminating at the ground and negative pin. This configuration is depicted in FIG. 17, in which the ribbon 120 is provided in a generally double helical configuration. The conductors 121 and 122 have both ends terminating in the power connector 125 at one end of the heater structure. The ribbon 120 loops back upon itself at the other end 124 of the heater structure.

With the pair of conductors provided along opposite edges of the ribbon the PTC material offers an amorphous array of parallel current paths along the entire length of the ribbon. Where the internal conduit temperature is lower the heater structure will have a lower resistance and more current will flow producing a greater heater effect. Where the internal temperature in the conduit is higher the PTC material will have a higher resistance, choking off current flow and reducing heating in that region of the conduit.

In a further aspect of the invention the PTC material is arranged in a parallel circuit over the length of the tube and forming part of the wall itself the full benefit of using PTC heater can be obtained. At the cold portions of the tube the material will have a lower resistance, which will result in more heat being dissipated in that area. Thus the tube will tend to regulate its own temperature.

In particular if the PTC material is composed to provide a threshold temperature at or just above the preferred gases temperature (eg above the dew-point of the humidified gases) the PTC material will maintain itself at that threshold temperature (with some hysteresis fluctuation) and condensation on the conduit surface will be at least substantially eliminated. This provides effective condensation control then maintaining an elevated temperature for the humidified gases where condensation may still form on the cold wall surfaces.

PTC material behaviour is exhibited in a range of polymer compositions with electrically conductive fillers. The behaviour can be characterised by a general statement that providing certain other conditions are fulfilled, the composition becomes electrically conductive when particles of electrically conductive filler form a continuous chain, penetrating the material from the point of entry of electric current to the place where it leaves the polymer material. Polymer compositions containing electrically conductive filler can exhibit PTC properties due to the formation of a chain of filler particles that are close enough for current to flow at a certain temperature, generating heat, which increases the temperature of the material until it reaches a phase transformation temperature. At the phase transformation temperature the crystalline polymer matrix changes to an amorphous structure. This change is accompanied by a small thermal expansion, forcing filler particles to move apart, breaking the conductive paths. Accordingly resistance rises sharply at this phase transformation temperature. As the material cools the small thermal conduction allows new conductive paths to form and current flow to resume. The rise and fall in temperature and the thermal contraction and expansion provides an inherent hysteresis in the cycle.

In producing a PTC material a number of factors have a bearing on the performance of the material. Particular factors include the quantity, type and particle size of the carbon black (or other conductive filler) used in the composite, the polymer that the carbon black binds with during mixing of the base materials and the process conditions such as temperature, pressure and time of mixing. It is important that the conductive filler particles are distributed evenly through the composite so that the composite exhibits uniform PTC behaviour.

For the present invention a PTC material having a phase transformation temperature not exceeding 40° C. is desired. One composition meeting these criteria has been developed and has the following composition:
- 20% by weight carbon black powder having a surface area of 254 m$^2$/g and oil Di-Butyl-Phthalate absorption of 188 cm$^3$/100 g. This powder is available as VULCAN XC-72 (powder) from Cabot Corporation.
- 64% Ethylene-Vinyl-Acetate. This material is available as ELVAX (grade 40w) from Dupont (E.I. du Pont de Nemours and Company), with a density of 965 kg per m$^3$, a melting point of 46° C. and melting index of 52.
- 13.5% Plastomer. An example plastomer is available as EXACT 2M055 from Exxon Mobil Corp, having a density of 882 kg/m$^3$, a melting point of 70° C. and a melting index of 3.
- 2.5% Wax.

This material was uniformly mixed and extruded to form a PTC ribbon with embedded conductors using a segmented screw extruder. The composite performance showed an acceptable level of self-regulation without the temperature exceeding 40° C.

There are many possible ways of producing a tube having a PTC wall material with a pair of conductors running the length of the tube to have all of the potential pathways through the PTC material operating in parallel. A number of preferred embodiments are now described.

Figure 18:
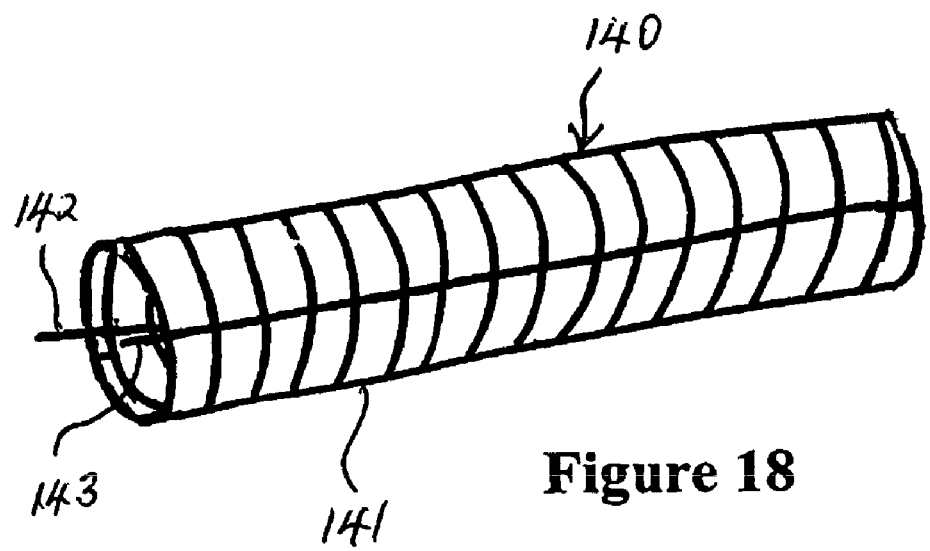
FIG. 18 is perspective view of a tube formed with a spirally wound PTC ribbon (without pre-embedded conductors) with longitudinally oriented conductors in the tube.

With reference to FIG. 18 a smooth walled tube 140 is shown by way of a first example. The smooth walled 140 tube has a PTC plastic material extruded as a narrow and thin ribbon 141 and wound helically with overlapping edges of adjacent turns. The edges of adjacent turns bound firmly to one another, fusing together in their molten state. A pair of conductors run 142, 143 longitudinally in the tube wall. The conductors are diametrically opposed. The conductors may be applied to either the internal or external surfaces of the molten PTC material during forming of the tube. To apply the conductors to the internal surface the conductors are applied longitudinally to the forming mandrel prior to laying the extruded PTC ribbon in place. Alternatively they may be applied directly to the outside of the PTC material while the material is still in a molten state. It would be appreciated that these conductors may also be applied helically rather than in a straight longitudinal direction, and that multiple conductors may be used.

Design of a PTC tube of this type involves selection of a wall thickness, a conductor gauge and a density of conductors in the PTC tube wall. The total resistance R (Ω) of the tube wall in its pre-threshold state will be a measure of the available power output for a given voltage. The available power output must be sufficient to offset the heat lose from the tube to its surrounding environment and (if the gases are entering the tube in a cooler state) to the humidified gases. The total resistance is proportional to the pre-threshold volume resistivity X (Ωm) of the material and to the average shortest path distance between the conductors of opposite plurality. The total resistance is also proportional to the inverse of the length $L_c$ (m) of the conductors and to the inverse of the wall thickness t(m) of the PTC material. Furthermore, typically there will be a pair of opposite and alternate paths for current to flow from a conductor of one polarity to the conductor of the other polarity, halving the total resistance. Thus the total resistance can be found from the formula:

$$R = \frac{X\overline{w}}{2L_c t}$$

where $\overline{w}$(m) is the average shortest length path between conductors.

Therefore for a given tube length and diameter the total cold resistance may be varied by varying the density of conductors (varying the average shortest path distance between conductors) or by varying the wall thickness. The density of conductors may be varied by adding additional conductors in parallel (eg: a second or more pair of conductors) or by disposing the conductors in a helical arrangement with decreasing pitch corresponding to an increased density. For a given tube diameter D(m) and tube length $L_T$(m) then the average shortest path length can be found using the total conductor path length for a single polarity (half the total conductor length) by:

$$\overline{w} = \frac{\pi D L_T}{2L_c}$$

The tube of FIG. 5 may be reinforced by applying a spiral bead, or by applying circumferential ribs to the outside of the tube, or by corrugating the tube, or by adding additional layers to the tube, particularly of a spiral ribbed or corrugated configuration, which would also provide additional external insulation from the ambient conditions.

Figure 19:
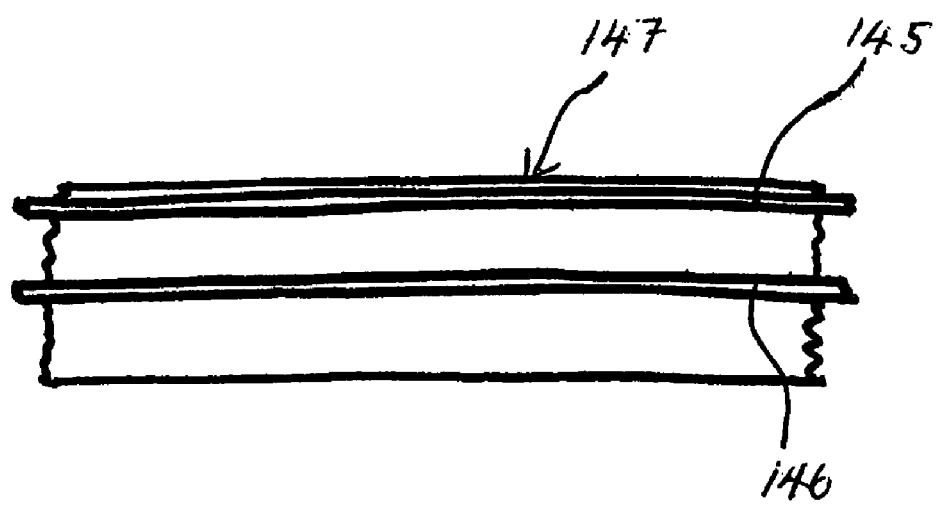
FIG. 19 is a plan view of a section of a ribbon of PTC material with a conductor embedded along one edge and second conductor embedded near the centre.
Figure 20:
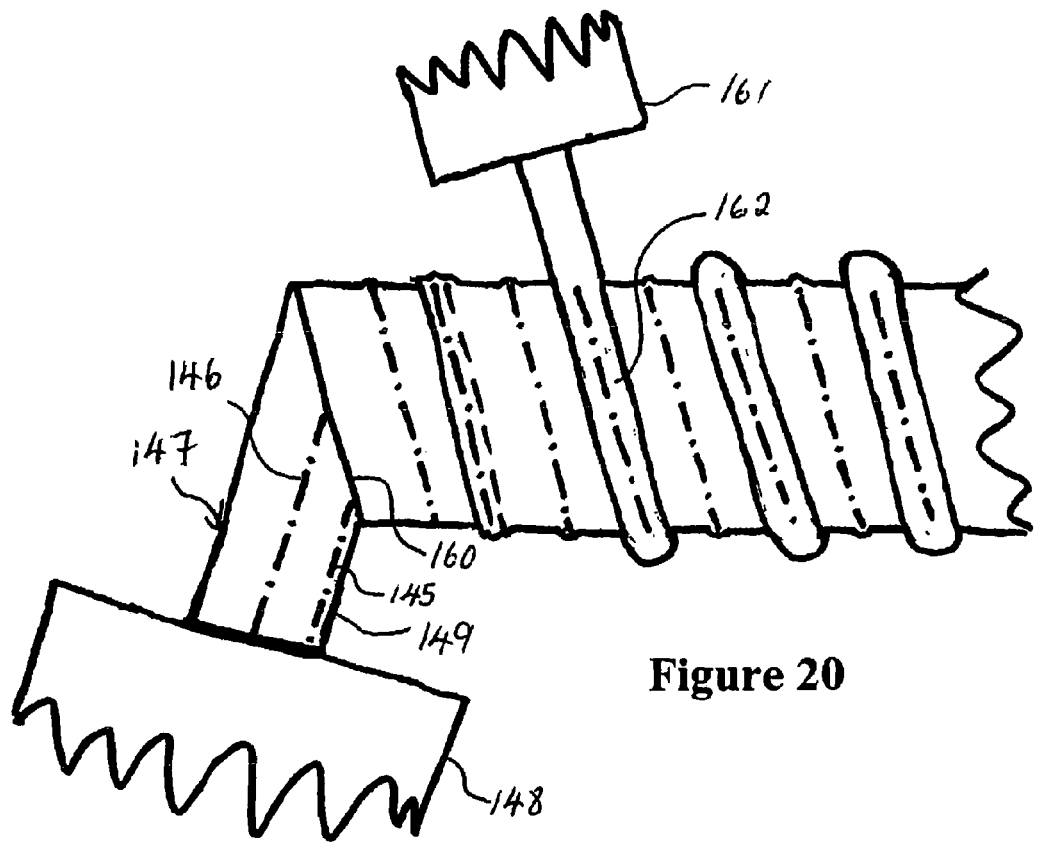
FIG. 20 is a plan view of a spiral forming arrangement performing a conduit using the ribbon of FIG. 16 (with the forming mandrel not shown)

A further construction is illustrated in FIGS. 19 and 20. FIG. 19 shows a pair of conductors 145, 146 extruded into a ribbon of PTC material. The first conductor 145 is disposed adjacent one edge of the PTC ribbon 147. The second conductor 146 is disposed adjacent the centre of the PTC ribbon 147. The exact location of the conductors within the PTC material is not critical, however the spacing between the conductors should be half of the pitch of winding the ribbon on to the former (eg: (width of ribbon−width of overlap between turns)÷2). For additional conductor density, additional pairs of conductors may be used. For lower conductor density the width of ribbon may be increased or alternatively a single conductor may be provided in the ribbon but two ribbons may be extruded and wound on to the former as a double helix.

Referring to FIG. 20 a manufacturing configuration is shown (without the rotating former, which may for example be a spiral pipeline mandrel available from OLMAS SRL of Italy). In this manufacturing configuration the PTC ribbon 147 is co-extruded with the embedded pair of conductors 145, 146 by a first extruder head 148. It is extruded directly on the former at a angle corresponding to the pitch of the former (the relationship between the advance and rotation speeds of tubes formed on it). The ribbon 147 is laid on the former so that the leading edge 149 of each new lap overlaps the trailing edge 150 of the immediately preceding turn. A reinforcing bead 162 is preferably extruded on to this overlap by an additional extruder head 161. The reinforcing bead 162 assists the bonding between overlapping turns of the ribbon as well as providing reinforcing against crushing of the formed tube.

Alternatively a conduit may be formed on a spiral pipeline mandrel with the reinforcing bead extruded to lie between the overlap of turns of the ribbon. This is particularly suited to where the ribbon is preformed and will not bond to itself without assistance. In this case contact may be provided between adjacent turns of the PTC ribbon along either side of the bead (for example by extended overlap) or the ribbon used may be have a conductor along each edge (as in FIG. 15).

Figure 21:
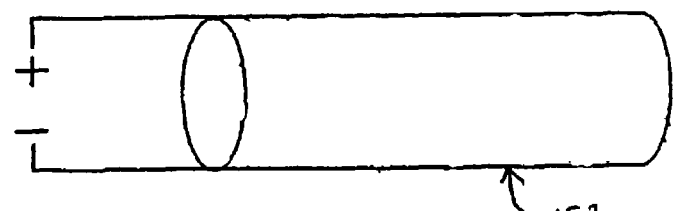
FIG. 21 shows construction of a tube incorporating flexible PTC elements in a parallel wire configuration.

FIG. 21 shows a further construction of a tube incorporating flexible PTC elements in a parallel wire configuration. The tube 158 is a flexible PTC material, which has two conductors built into it. The tube 158 according to this construction may be a directly extruded tube with the conductors co-extruded into the tube wall, or alternatively the conductors may be added subsequent to forming the tube by direct application to the exterior of the tube as wires or as conductive ink. The tube may have an outer layer (not shown), which provides electrical insulation and thermal insulation to the tube. The tube may be corrugated by passing through a set of corrugating rollers, to provide flexibility and lateral reinforcing against crushing.

The tube with PTC wall material allows the insufflating and humidifying system to be used without any sensor at the patient airway or at the humidifier. FIG. 1 shows a humidifier configuration using a PTC tube. If the PTC tube is used in relation to the system shown in FIG. 1 replacing conduit 3, gas would enter the humidification chamber 9 via inlet port 12 and is humidified by water 15 and heated by heater plate 16. An absolute humidity sensor 155 (located at the humidifier end of the conduit 3) controls the heater plate so that the gas passing sensor 155 is at a desired level of absolute humidity. PTC tube 3 is heated by an external voltage (not shown) so that the internal surface temperature is at a constant desired temperature, which is selected to be above the dewpoint of the gas. The gas, which leaves tube 3 at outlet 157, will therefore be near the temperature of the tube, and containing the desired level of absolute humidity, which was controlled by absolute humidity sensor 155.

Heated Wall Tube

Figure 22:
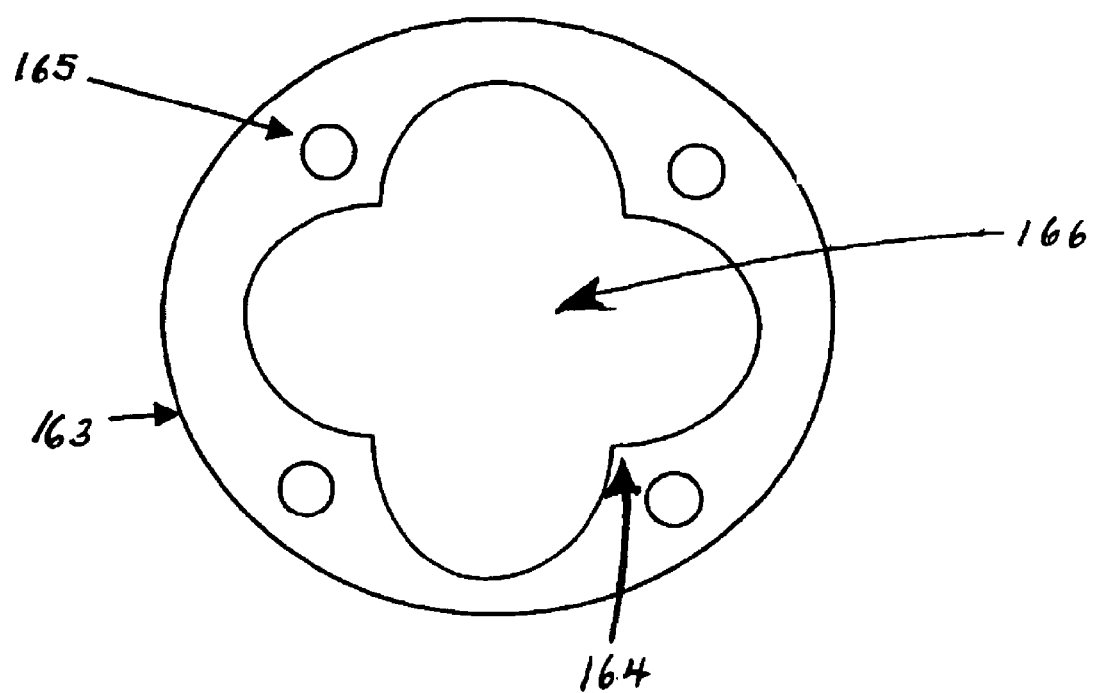
FIG. 22 shows cross-sectional view of a further embodiment of the transportation means that may be used with the apparatus of the present invention, the transportation means is a conduit having heater wires extruded within the conduit walls.

As an alternative to the tube 33 and spiral heater wire 36 that makes up the transportation means as described with reference to FIG. 6, the present invention may be provided with a transportation means that comprises a conduit having wires extruded within the tubing walls. Referring to FIG. 22 the conduit 163, made of an appropriate plastics material, such as a flexible polymer, has ridges or ribs 164 extruded into the inner wall of the conduit. Each rib extends towards the centre of the conduit and has moulded into it along the conduit's length a heater wire 165. Each heater wire 165 is made from copper, copper alloy or made from any other appropriate electricity conducting material, such as a PTC material, and is moulded within the ribs at the time the polymer conduit is moulded.

Although FIG. 22 shows a conduit 163 with four ribs 164 in the inner wall of the conduit 163, the conduit may be provided with any number of ribs that is practicable. Also, the number of heater wires 165 may not correspond with the number of ribs provided in the conduit inner wall.

A conduit in this embodiment enables the gases flowing through the centre 166 of the conduit to the body cavity, to be heated and maintains an appropriate moisture content and thus gases humidity. Furthermore, the ribs 164 provide the added advantage that if the conduit is pressed, crushed or bent the ribs provide for the maintaining of an area, even if that area is somewhat reduced, within the conduit so that gases flow is maintained.

What is claimed is:

1. An apparatus for preparing and delivering insufflation gases used to inflate a portion of a patient during an endoscopic or laparoscopic procedure, said apparatus comprising:
    a humidifier located proximate to a gas supply and distant from the patient, said humidifier in fluid communication with said gas supply;
    a gas delivery conduit connected to and in fluid communication with an outlet of said humidifier, said conduit having a length of about 3 to about 6 feet to permit said humidifier to be located outside an operating sterile zone, said conduit comprising a heating element for heating said gases as said gases move through said conduit; and
    a gas delivery device in fluid communication with said conduit and configured to deliver said gases to the patient.

2. The apparatus of claim 1, further comprising a gas supply co-located in a housing with said humidifier.

3. The apparatus of claim 1, wherein said humidifier is located at least about 3 to about 6 feet from the patient.

4. The apparatus of claim 1, wherein said gas supply is an insufflator configured to receive gases from a gas source and control a pressure and a volumetric flow rate of the gases.

5. The apparatus of claim 4, wherein said gas source is a gas cylinder.

6. The apparatus of claim 4, wherein said gas source is a gas outlet.

7. The apparatus of claim 4, further comprising a filter located between the gas source and the insufflator.

8. The apparatus of claim 4, further comprising a pressure sensor adapted to measure pressure of gases passing through the insufflator, an audible alarm, and a controller configured to receive data from the pressure sensor and provide output to the audible alarm, wherein the audible alarm is configured to sound if the pressure of the gases passing through the insufflator exceeds a threshold.

9. The apparatus of claim 1, wherein said humidifier comprises:
    a chamber having an inlet and an outlet, said chamber adapted to contain a volume of water;
    a heater configured to heat the volume of water within said chamber; and
    a controller configured to selectively energize the heater to heat the volume of water and cause at least some of the volume of water to become water vapor;
    wherein, in use, gases passing through the chamber from the inlet to the outlet are humidified by the water vapor.

10. The apparatus of claim 9, wherein said inlet is in fluid communication with said gas supply.

11. The apparatus of claim 9, wherein a first end of said gas delivery conduit is coupled to said outlet and a second end of said conduit is coupled to said gas delivery device.

12. The apparatus of claim 1, wherein at least a portion of a wall of said gas delivery conduit comprises at least a layer of positive temperature coefficient material having a local electrical resistance positively related to a local temperature.

13. The apparatus of claim 12, wherein a phase transformation temperature of said positive temperature coefficient material is within 5° C. of a temperature of gases leaving said humidifier.

14. The apparatus of claim 12, wherein a phase transformation temperature of said positive temperature coefficient material is above the temperature of said gases leaving said humidifier and below 40° C.

15. The apparatus of claim 1, wherein said gas delivery device comprises a cannula configured to be inserted in an incision in the patient.

16. The apparatus of claim 1, wherein said gas delivery device comprises an oral interface comprising:
   a vestibular shield having an inner surface and an outer surface, said vestibular shield having a predetermined height configured to overlap the patient's teeth and gums when positioned in a mouth vestibule of the patient;
   a gas passageway extending from said outer surface of said vestibular shield to said inner surface of said vestibular shield for allowing the passage of gases through said oral interface;
   an extra-oral seal associated with said gas passageway, said seal having a first configuration substantially unengaged with the patient's face when said shield is inserted into the patient's mouth and a second configuration substantially engaged with the patient's face when correctly positioned in the patient's mouth; and
   an oral interface connector located on said gas passageway and configured to connect said interface to said gas delivery conduit.

17. The apparatus of claim 1, wherein said gas delivery device comprises a rectal interface comprising:
   a substantially tubular body;
   a flange extending from an outer surface of said tubular body; and
   a rectal interface connector configured to connect said rectal interface to said gas delivery conduit.

18. An apparatus for preparing and delivering insufflation gases used to inflate a portion of a patient during an endoscopic or laparoscopic procedure, said apparatus comprising:
   a humidifier located proximate a gases supply and distant from the patient and including an adjustable heater adapted to regulate the temperature and humidity of said insufflation gases, said humidifier in fluid communication with said gas supply;
   a gas delivery conduit connected to and in fluid communication with an outlet of said humidifier, said conduit having a length of about 3 to about 6 feet to permit said humidifier to be located outside an operating sterile zone, said conduit comprising a heating element for heating said gases as said gases move through said conduit;
   a sensor adapted to measure a property of said insufflation gases being delivered to said patient; and
   a controller adapted to receive a signal representative of said measured property from said sensor;
   wherein, in use, the controller regulates the temperature and humidity of the insufflation gases entering the patient by controlling the adjustable heater of the humidifier and the heating element of the gas delivery conduit based on the signal from the sensor.

19. The apparatus of claim 18, wherein said humidifier is located at least about 3 to about 6 feet from the patient.

20. The apparatus of claim 18, wherein said humidifier comprises:
   a chamber having an inlet and an outlet, said chamber adapted to contain a volume of water and said adjustable heater configured to heat the volume of water within said chamber; and
   a controller configured to selectively energize the heater to heat the volume of water and cause at least some of the volume of water to become water vapor;
   wherein, in use, gases passing through the chamber from the inlet to the outlet are humidified by the water vapor.

21. An apparatus for preparing and delivering gases used in a medical procedure involving a patient, said apparatus comprising:
   a humidifier located proximate to a gas supply and distant from the patient, said humidifier in fluid communication with said gas supply;
   a filter located between the humidifier and the gas supply such that gases leaving the gas supply pass through said filter before entering the humidifier;
   a gas delivery conduit connected to and in fluid communication with an outlet of said humidifier, said conduit being sufficiently long to permit the humidifier to be located outside an operating sterile zone, said conduit comprising a heating element for heating the gases as the gases move through said conduit; and
   a gas delivery device in fluid communication with the conduit and configured to deliver the gases to the patient.

22. The apparatus of claim 21, wherein said gas supply is an insufflator configured to receive gases from a gas source and control a pressure and a volumetric flow rate of the gases.

23. The apparatus of claim 22, wherein said gas source is a gas cylinder.

24. The apparatus of claim 22, wherein said gas source is a gas outlet.

* * * * *